(12) United States Patent
Mooney et al.

(10) Patent No.: US 7,250,099 B2
(45) Date of Patent: Jul. 31, 2007

(54) OPTICAL DETECTION ALIGNMENT COUPLING APPARATUS

(75) Inventors: Paul Mooney, Rancho Santa Margarita, CA (US); Varouj Amirkhanian, La Crescenta, CA (US)

(73) Assignee: Biocal Technology, Inc., Irvine, CA (US)

( * ) Notice: Subject to any disclaimer, the term of this patent is extended or adjusted under 35 U.S.C. 154(b) by 406 days.

(21) Appl. No.: 10/319,803

(22) Filed: Dec. 13, 2002

(65) Prior Publication Data
US 2004/0115648 A1 Jun. 17, 2004

(51) Int. Cl.
G01N 21/64 (2006.01)

(52) U.S. Cl. ............ 204/603; 204/452; 356/344; 356/440

(58) Field of Classification Search ......... 204/452, 204/603; 356/440, 344, 410, 411
See application file for complete search history.

(56) References Cited

U.S. PATENT DOCUMENTS 5,430,541 A * 7/1995 Sapp et al. ............ 356/246
5,434,664 A * 7/1995 Sapp ..................... 356/244
5,605,666 A * 2/1997 Goodale et al. ......... 422/103
6,184,990 B1 * 2/2001 Amirkhanian et al. ... 356/440

FOREIGN PATENT DOCUMENTS

| CA | 2348359 | 11/2002 |
|----|---------|---------|
| EP | 0021499 | 1/1981 |
| WO | WO 02/28509 | 4/2002 |
| WO | WO 02/059589 | 8/2002 |

OTHER PUBLICATIONS

International Search Report of Counterpart PCT Application No. PCT/US03/39971.
Partial International Search Report of Counterpart PCT Application No. PCT/US2004/043424.

* cited by examiner

*Primary Examiner*—Kaj K. Olsen
(74) *Attorney, Agent, or Firm*—Liu & Liu

(57) ABSTRACT

An apparatus for aligning a capillary column with one or more excitation fibers and with one or more optical lens elements for Capillary Electrophoresis. The apparatus includes two identical blocks having a plurality of grooves for positioning and aligning the capillary column with the one or more excitation fibers, and a plurality of lens seats for optically coupling the lens element with the capillary column. Each block includes a male and female part for mating the two identical blocks together.

25 Claims, 18 Drawing Sheets

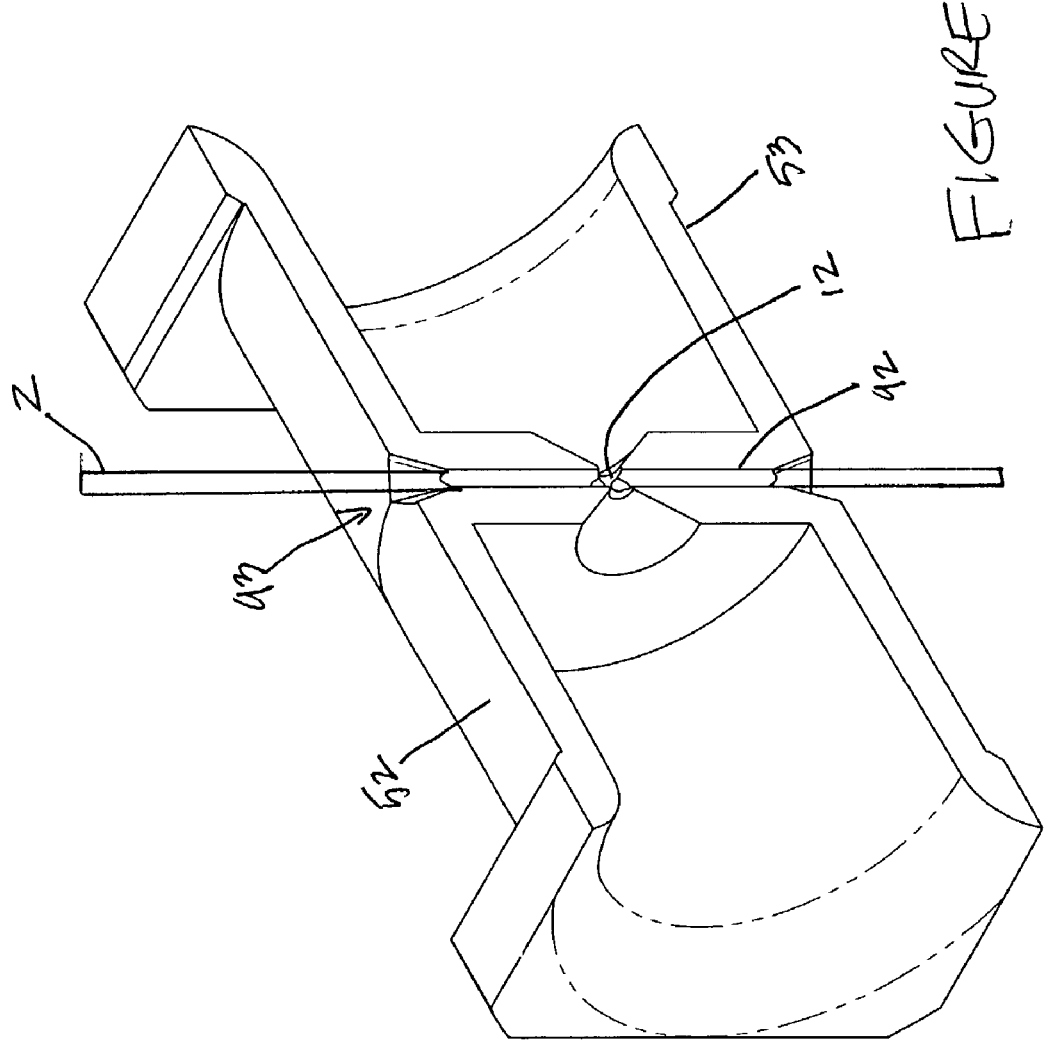

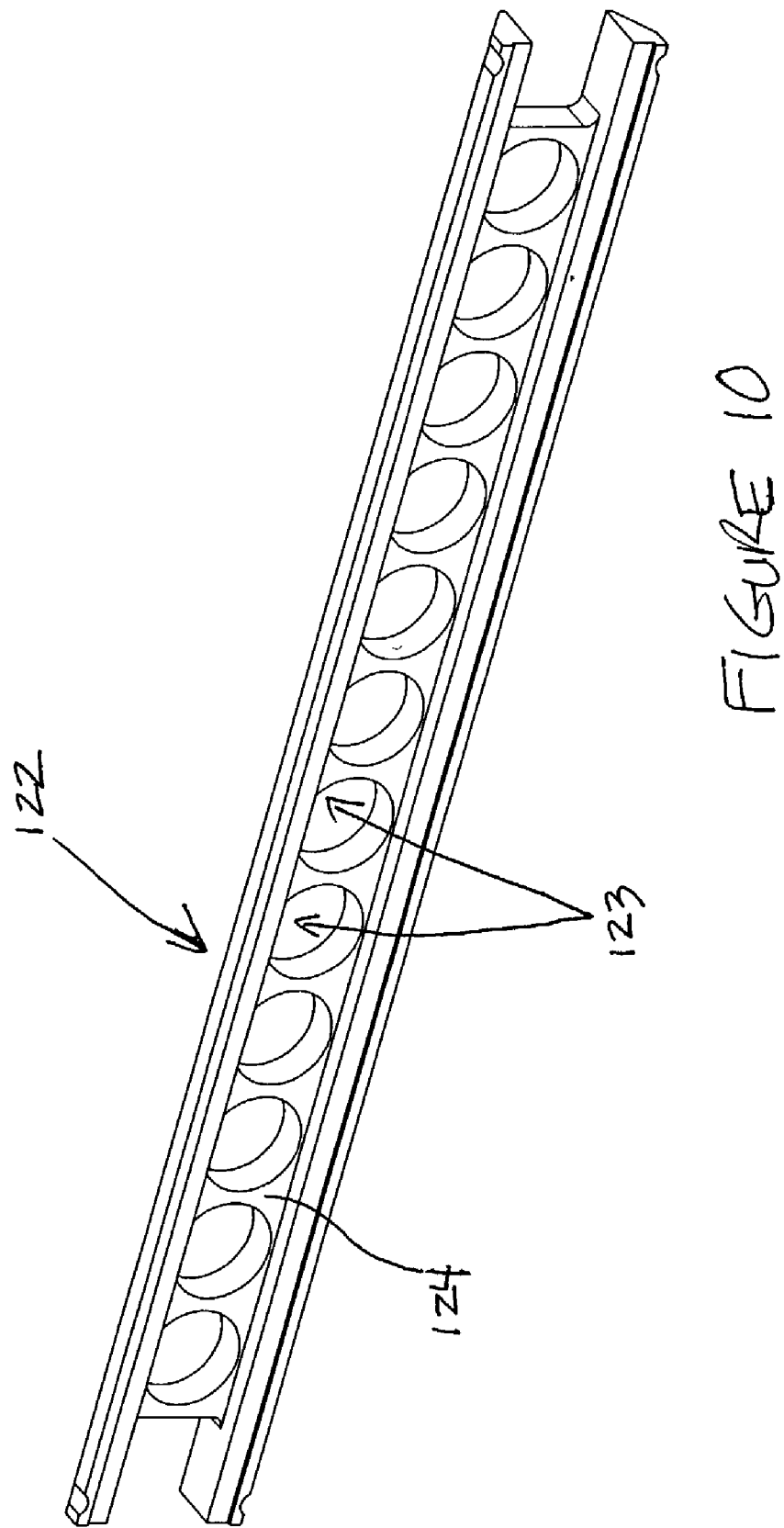

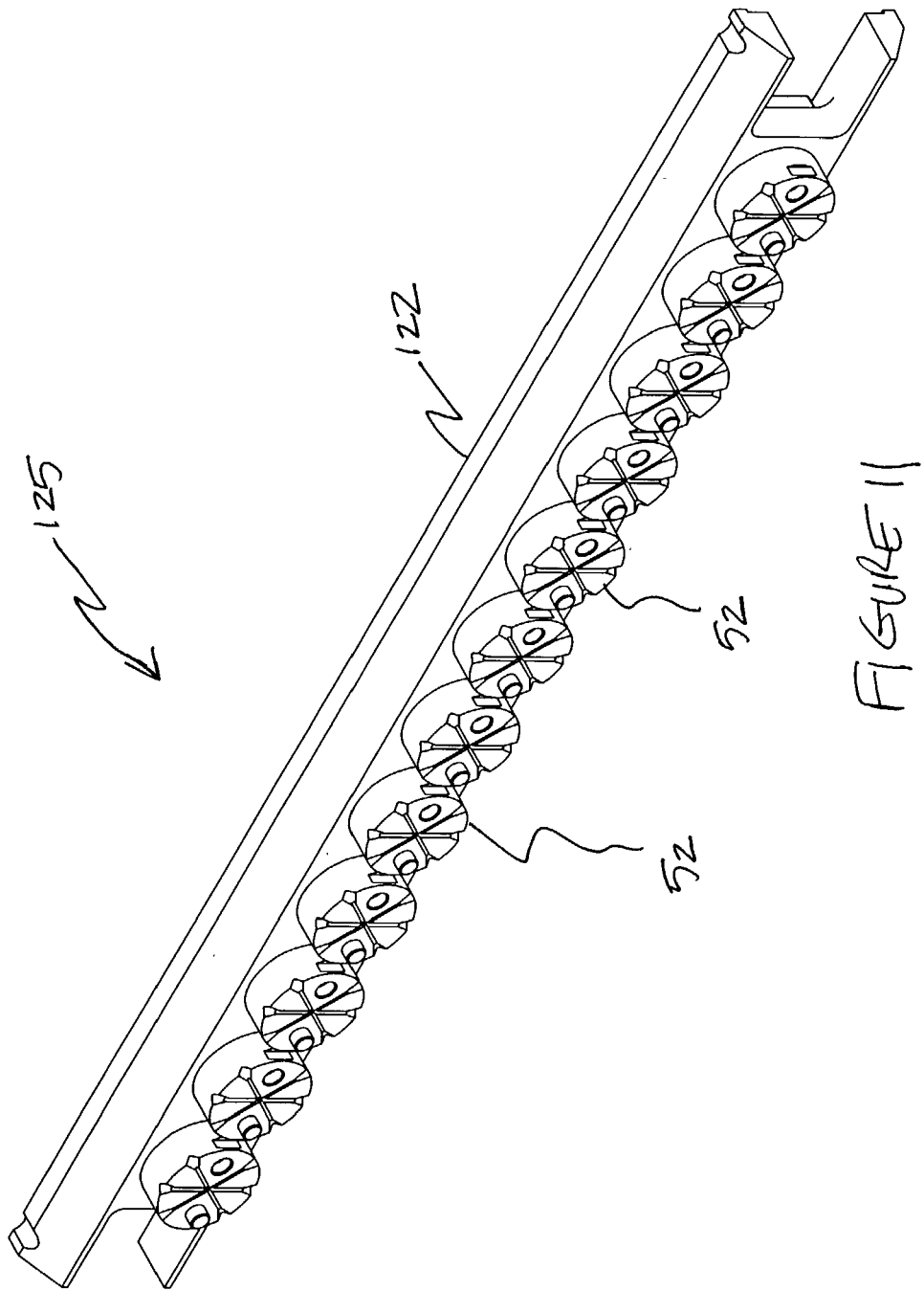

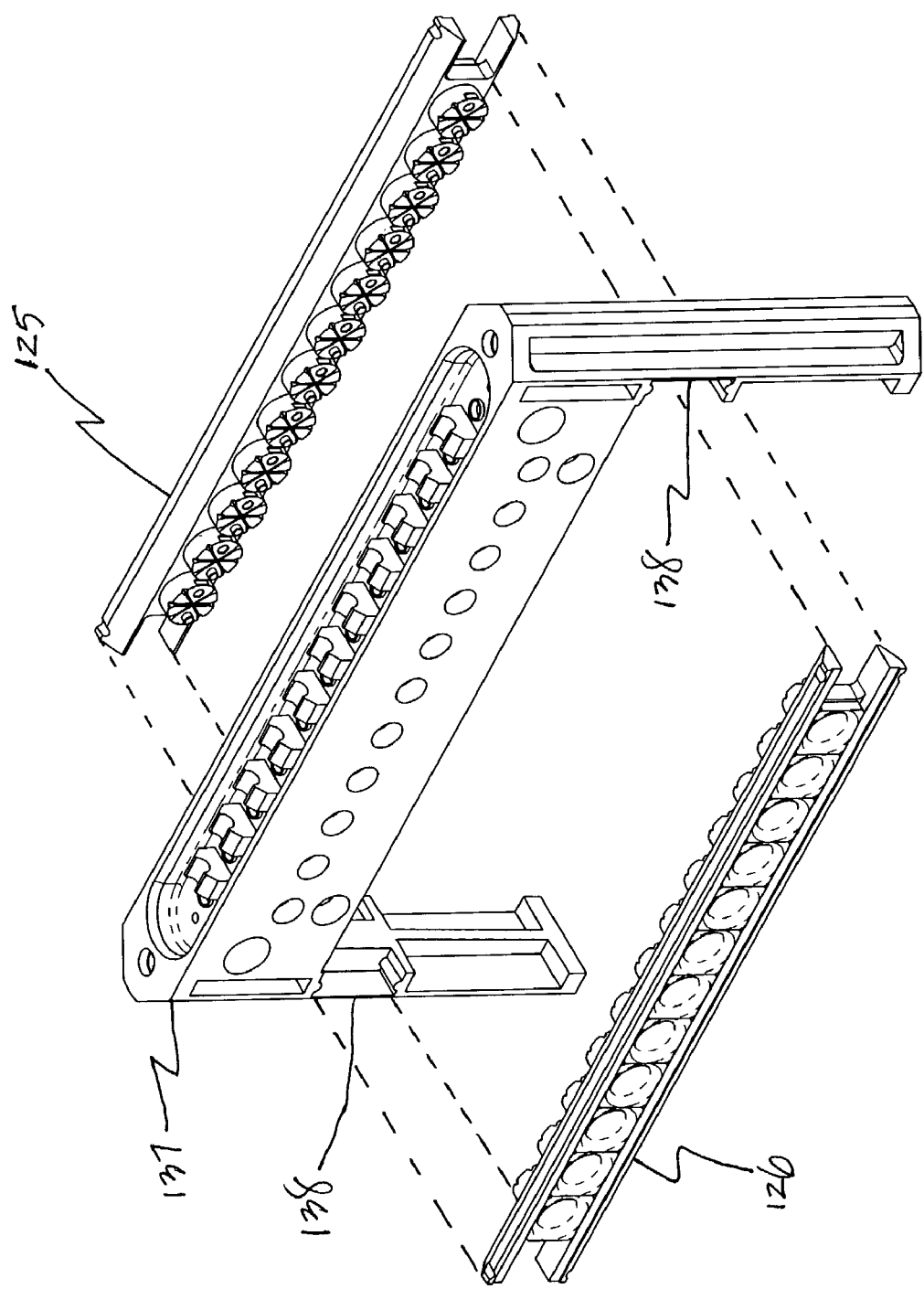

OPTICAL DETECTION ALIGNMENT COUPLING APPARATUS

BACKGROUND OF THE INVENTION

1. Field of the Invention

The present invention relates to bio-separation systems, and more particularly a coupler for aligning optical detection components.

2. Description of Related Art

Bioanalysis, such as DNA analysis, is rapidly making the transition from a purely scientific quest for accuracy to a routine procedure with increased, proven dependability. Medical researchers, pharmacologists, and forensic investigators all use DNA analysis in the pursuit of their tasks. Yet due to the complexity of the equipment that detects and measures DNA samples and the difficulty in preparing the samples, the existing DNA analysis procedures are often time-consuming and expensive. It is therefore desirable to reduce the size, number of parts, and cost of equipment, to ease sample handling during the process, and in general, to have a simplified, low cost, high sensitivity detector.

One type of DNA analysis instrument separates DNA molecules by relying on electrophoresis. The term electrophoresis refers to the movement of a charged molecule under the influence of an electric field. Electrophoresis can be used to separate molecules that have equivalent charge-to-mass ratios but different masses. DNA fragments are one example of such molecules. Electrophoresis techniques could be used to separate fragments of DNA for genotyping applications, including human identity testing, expression analysis, pathogen detection, mutation detection, and pharmacogenetics studies.

There are a variety of commercially available instruments applying electrophoresis to analyze DNA. One such type is a capillary electrophoresis (CE) instrument. CE instruments employ a fused silica capillary column carrying a buffer solution. A DNA sample is capable of being introduced through the capillary column by electrophoresis. When electrophoresis is applied to the capillary column, the DNA sample separates into its components, and the components migrate through the capillary column to a detection window where the DNA components can be analyzed.

There are detection techniques well known in the art for analyzing the DNA components. Radiation absorption detection is one such well-known technique that involves directing incident radiation at the analytes in the detection window and measuring the amount or intensity of radiation that passes through the analytes, or the equivalent decrease in intensity or the amount of radiation that is absorbed by the analytes (i.e., the attenuation of the incident radiation).

Another well-known detection technique is Emissive radiation detection. Fluorescence detection, such as Laser-induced fluorescence (LIF) detection methods, is often the detection method of choice in the fields of genomics and proteomics because of its outstanding sensitivity compared to other detection methods. The DNA sample is tagged with a fluorescent material. The DNA components can be analyzed by directing light through the capillary wall at the detection window, at the tagged components, and detecting the fluorescence emissions induced by the incident light. The intensities of the emission are representative of the concentration, amount and/or size of the components of the sample.

There are numerous challenges in designing CE-based instruments and CE analysis protocols. To maximize signal intensity and sensitivity and resolution of detection, the precise position and alignment of particular CE instrument components, such as the capillary column, the excitation light fiber and the detection lens, with respect to each other are critical design concerns. The capillaries used in CE are relatively small, ranging in size from 20 $\mu$m to 250 $\mu$m I.D., and CE requires that the detection window/zone be small enough to reduce the scattered background/excitation, lower the baseline Noise, increase Signal/Noise ratio and improve detection sensitivity. It is critical for the excitation fiber to be precisely positioned and aligned such that a substantial portion of the light beam is directed through the capillary wall at the separated sample components in the capillary bore. Otherwise, the light can scatter at the outside capillary wall/air interface and inside capillary wall/buffer interface (Raman scattering), which can obscure or corrupt the fluorescence emission intensity. The problem can be multiplied if more than one fiber is used. Therefore, having one or more excitation fiber positioned and aligned precisely with the detection window is desirable.

Additionally, sample size and background noise pose additional concerns in designing CE-based instruments. Only a relatively small amount of DNA sample is being analyzed at any given time. As such, the small sample emits fluorescence signals at levels that compete with background noise. The background noise can come from the light source, from Raman scattering, or from the materials of other instrument components. The fluorescence signal can also scatter at the wall interfaces. One or more lenses have been used to increase detection sensitivity. However, a small misalignment of the detection lens can have large effects on the detection sensitivity. Accordingly, it is desirable for one or more detection lens elements to be precisely positioned and aligned with the detection window. Furthermore, having instrument components made from materials that minimize background noise is desirable.

In the past, various techniques were developed for more completely collecting the fluorescence emissions to improve signal intensity and hence detection sensitivity. These techniques involved additional moving and non-moving components that added to the relative complexity and cost of the detection setup. Therefore, it is desirable to have a means for CE analyses that is versatile enough for use in a laboratory setting as well as being capable of incorporation into a CE-based instrument capable of various detection techniques. Additionally, this also calls for a means of producing and assembling instruments at low cost.

SUMMARY OF THE INVENTION

The present invention provides an apparatus for precisely aligning the optical detection components of a bio-separation system. In a capillary electrophoresis (CE) system, for example, the apparatus facilitates alignment of a capillary, one or more excitation fibers, and one or more optical lens elements for detection. In one aspect of the present invention, the apparatus is capable of aligning the capillary relative to one or more excitation fibers and relative to one or more optical lens elements. The apparatus comprises an alignment block for aligning the capillary, the fibers and the lens elements with respect to each other and a support block for maintaining these components in alignment. The alignment block includes a plurality of grooves for aligning the one or more fibers with respect to a detection window of the capillary. The support block can mate with the alignment block to maintain the capillary and the one or more fibers within the grooves. The apparatus also includes a lens seat on the alignment block for optically aligning the optical axis of the lens element with respect to the capillary axis and fiber(s) axis. By supporting multiple excitation fibers and multiple lens elements, the apparatus can be adapted for numerous CE detection schemes (e.g., fluorescence or absorbance type detections).

In another aspect of the present invention, the apparatus includes the alignment and the support blocks being identical blocks capable of mating with each other for assembly into the apparatus. Each block includes a plurality of grooves that form a plurality of shafts for aligning the excitation fibers with respect to the capillary when the blocks have mated, and a lens seat for optically aligning the lens element with the capillary. Furthermore, each block includes a locking mechanism having a male part and a female part. The male part of one block can mate in a press fit with the corresponding female part of the other block, which provides easy assembly of the apparatus without fasteners. Additionally, the locking mechanism provides a means for aligning the two blocks with respect to each other.

In a further aspect of the present invention, an assembly of a linear array of apparatuses is provided for incorporation into a multi-capillary CE instrument. The assembly includes a bracket capable of supporting a plurality of apparatuses in a linear array. The assembly can further be incorporated in a cartridge for use in a multi-capillary CE system.

BRIEF DESCRIPTION OF THE DRAWINGS

For a fuller understanding of the nature and advantages of the invention, as well as the preferred mode of use, reference should be made to the following detailed description read in conjunction with the accompanying drawings. In the following drawings, like reference numerals designate like or similar parts throughout the drawings.

FIG. 8 is a cross-sectional view of the alignment apparatus shown in FIG. 2 taken along line 8-8.

FIG. 10 is a perspective view of a linear array support bracket in accordance with one embodiment of the present invention.

FIG. 11 is a perspective view of an assembly of a linear array of alignment blocks.

FIG. 15 is an exploded perspective view of a mid-section body of a multi-capillary cartridge, the assembly of the linear array of alignment blocks and the assembly of the linear array of support blocks.

DETAILED DESCRIPTION OF THE PREFERRED EMBODIMENTS

This invention is described below in reference to various embodiments with reference to the figures. While this invention is described in terms of the best mode for achieving this invention's objectives, it will be appreciated by those skilled in the art that variations may be accomplished in view of these teachings without deviating from the spirit or scope of the invention.

The present invention is directed towards a novel apparatus for precisely aligning components of a CE system, including a capillary column, one or more excitation fibers, and one or more optical lens elements. For the purpose of illustrating the principles of the present invention and not by limitation, the present invention is described by reference to embodiments directed to capillary electrophoresis and radiation induced fluorescence.

Figure 1:
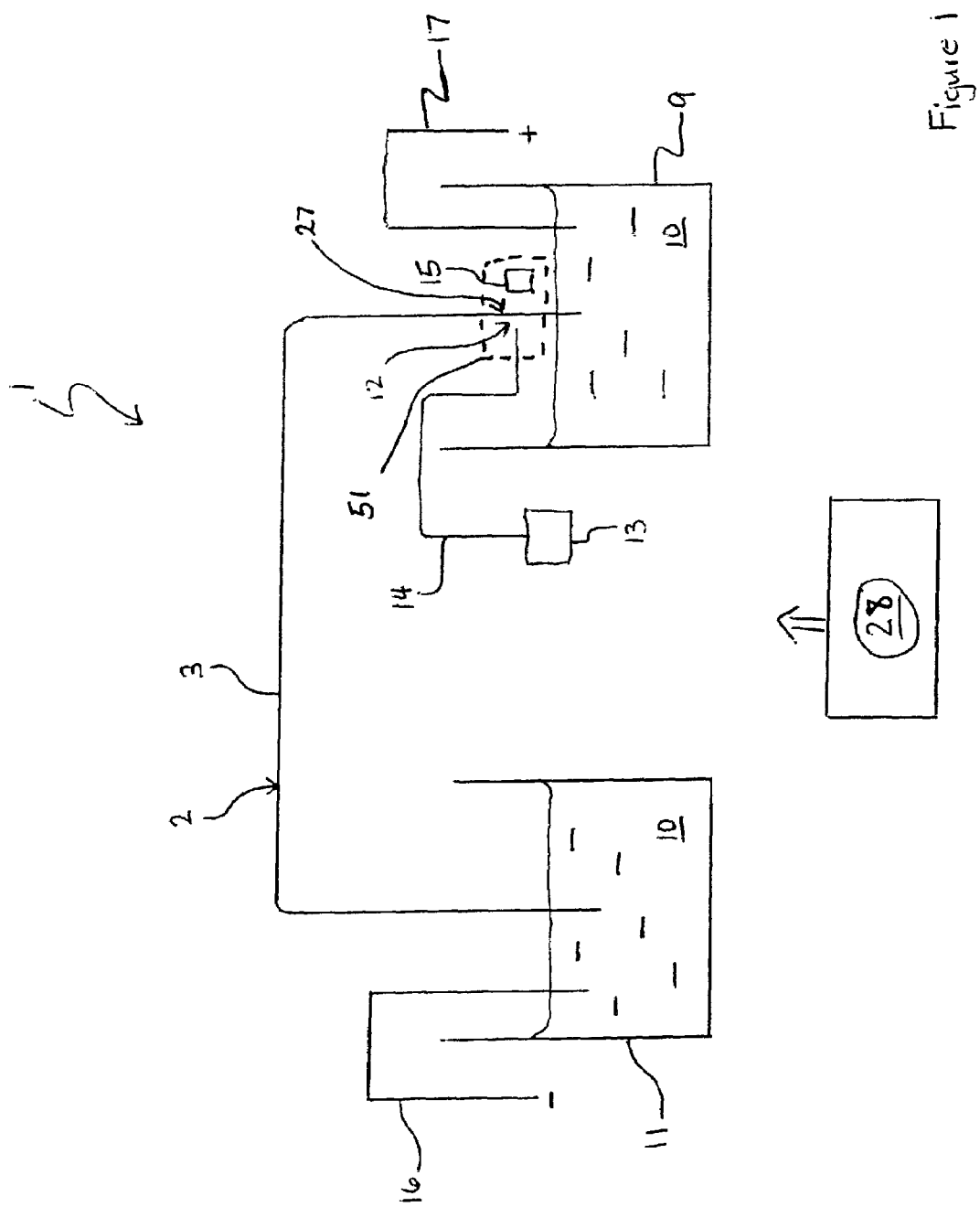
FIG. 1 is a schematic view of a capillary electrophoresis system.

Referring to FIG. 1, a bio-separation system, and more specifically a capillary electrophoresis (CE) system 1, is schematically illustrated. The CE system 1 generally comprises a capillary separation column 2 (e.g., 200-500 μm O.D.), which defines a micro-bore separation channel 3 (e.g., 20-250 μm I.D.). The capillary column 2 may be made of fused silica, glass, polyimide, or other plastic/ceramic/glassy materials. The inside walls of the capillary 2 (i.e., the walls of the separation channel 3) may be coated with a material that can build up an electrostatic charge to facilitate electrophoresis and/or electrokinetic migration of the sample components. The separation channel 3 may be filled with a separation support medium, which may simply be a running buffer, or a sieving gel matrix well known in the art. For radiation induced fluorescence detection, the gel matrix includes a known fluorophore, such as Ethidium Bromide.

One end of the capillary 2 is submerged in a reservoir 9 of running buffer/gel 10, and the other end of the capillary 2 is coupled to a sample vial 11. The capillary 2 is provided with a detection window 12. The detection window 12 is a section of the separation channel 3 wherein the Polyimide coating is pre-burned or removed to define a transparent section of the separation channel 3. The detection window 12 can be located at an end section of the capillary 2 near to the gel-reservoir 9. Radiation from a radiation source 13 (e.g., LED or laser), which is part of a sample analysis system, is carried through an excitation fiber 14 and is directed from outside the capillary 2 through the detection window 12 at the analytes. A radiation detector 15, also part of the sample analysis system, is positioned outside the detection window 12. Electrodes 16 and 17 are coupled to the buffer reservoir 11 and gel reservoir 9 to complete the electrophoresis path.

For the sake of completeness, it is sufficient to briefly mention the operation of the CE system 1. In operation, a prepared biological sample (e.g., a DNA sample), direct from a Polymerase Chain Reaction (PCR) machine is introduced into the far end of the capillary 2 away from the detection window 12 by any of a number of ways that is not part of the present invention (e.g., electrokinetic injection from a sample reservoir or physical pressure injection using a syringe pump). The sample binds to the fluorophore.

When a DC potential (e.g., 1-30 KV) is applied between electrodes 16 and 17, the sample migrates under the applied electric potential along the separation channel 3 (e.g. DNA that is negatively charged travels through the sieving gel with an integrated dye matrix/fluorophore toward a positive electrode as shown in FIG. 1) and separates into bands of sample components. The extent of separation and distance moved along the separation channel 3 depends on a number of factors, such as migration mobility of the sample components, the mass and size or length of the sample components, and the separation support medium. The driving forces in the separation channel 3 for the separation of samples could be electrophoretic, pressure, or electro-osmotic flow (EOF) means.

When the sample reaches a detection zone 27 within the detection window 12, excitation radiation is directed via the excitation fiber 14 at the detection zone 27. The sample components fluoresce with intensities proportional to the concentrations of the respective sample components (proportional to the amount of fluorescent tag material). The radiation detector 15 detects the intensities of the emitted fluorescence at a wavelength different from that of the incident radiation. The detected emitted radiation may be analyzed by known methods. The detection zone 27 is not necessarily a well-defined zone with well-defined boundaries. This is due to the nature of the sample, the incident radiation and the radiation emission. The detection zone 27 is generally a zone wherein radiation from the excitation fiber 14 is directed and from where radiation emission from the radiated sample originates. For an automated system, a controller 28 controls the operations of the CE system 1.

Figure 2:
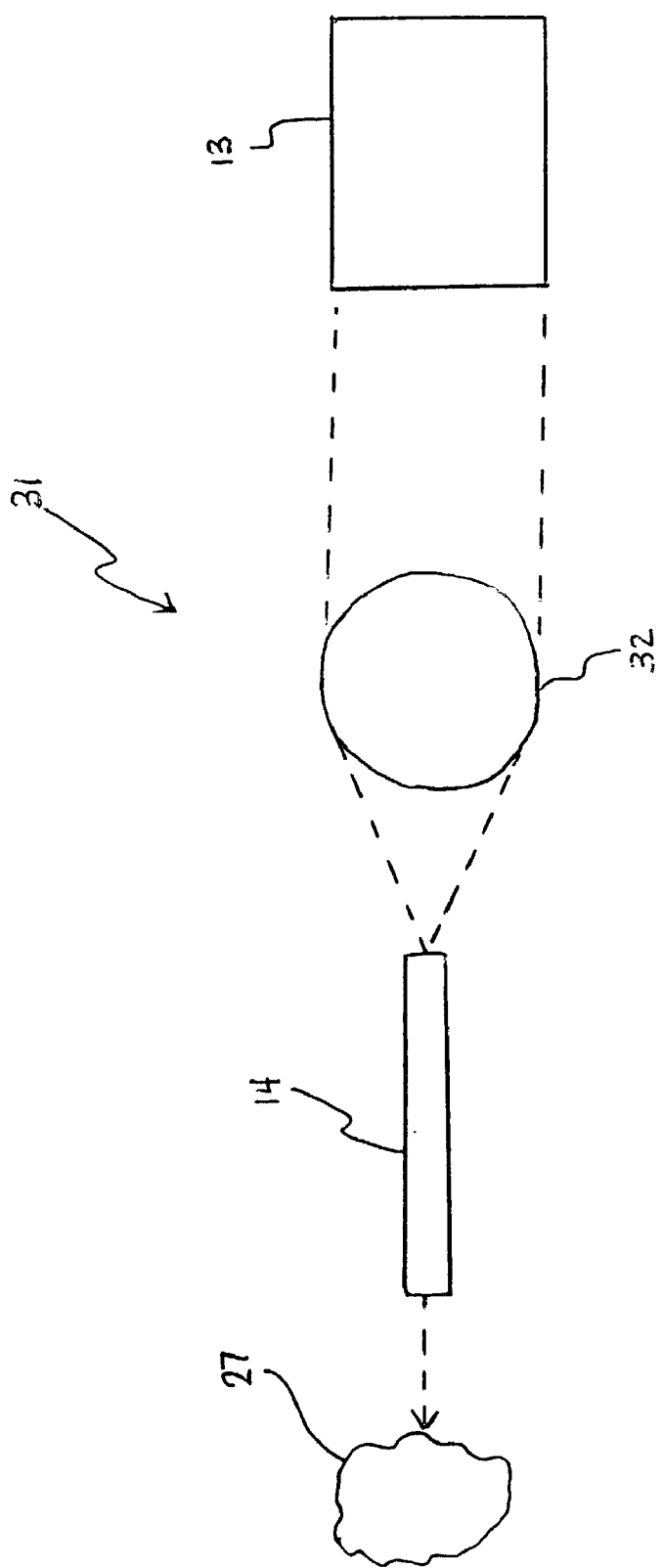
FIG. 2 is a schematic view of the excitation system.

The CE system 1 includes an excitation system 31 for providing and directing radiation at the separated DNA fragments within the detection zone 27. FIG. 2 is a schematic view of the excitation system 31. The excitation system 31 includes the radiation or light source 13, a coupling lens (e.g. micro-ball lens) 32, and the excitation fiber 14.

The light source 13 can be a fluorescence excitation light source such as an LED or a laser. The attractive features of LED's as light sources are their low cost, small size, long lifetime, good intensity and stability resulting in low noise, and the possibility of direct electronic modulation of the intensity. The LED's can be based on InGaN material technology (e.g., HLMP-CB15 and HLMP-CM15 from Agilent) with an average light output power of 2.5-3 mW. Different color LED's (e.g., blue or green LED's) could be used as excitation sources for excitation of different fluorophores (different applications). The light from the LED's can be in wavelength ranges of 300-900 nm, and specifically at 524 nm. Surface Mount (SMT) type LED's could also be used.

The excitation light source 13 can also be Laser Diodes (semiconductor solid-state lasers) in the range of 400-800 nm. Alternatively, they could be pulsed lasers (e.g., solid state lasers, gas lasers, dye lasers, fiber lasers).

The excitation system 31 includes the micro-ball lens 32 and the excitation fiber 14. The micro-ball lens 32 couples the light from the radiation source 13 (i.e., the LED or laser) to enter the excitation fiber 14. The excitation fiber 14 receives the light from the lens 32 and directs the light to the detection zone 27. The excitation fiber 14 can be a light transmitting optical fiber (e.g., multi-mode silica or plastic 200 micron Core fibers, 0.22 N.A.). The Numerical Aperture (N.A.) of the excitation fiber 14 determines the amount of power density launched into the gel close to the detection zone 27.

Figure 3:
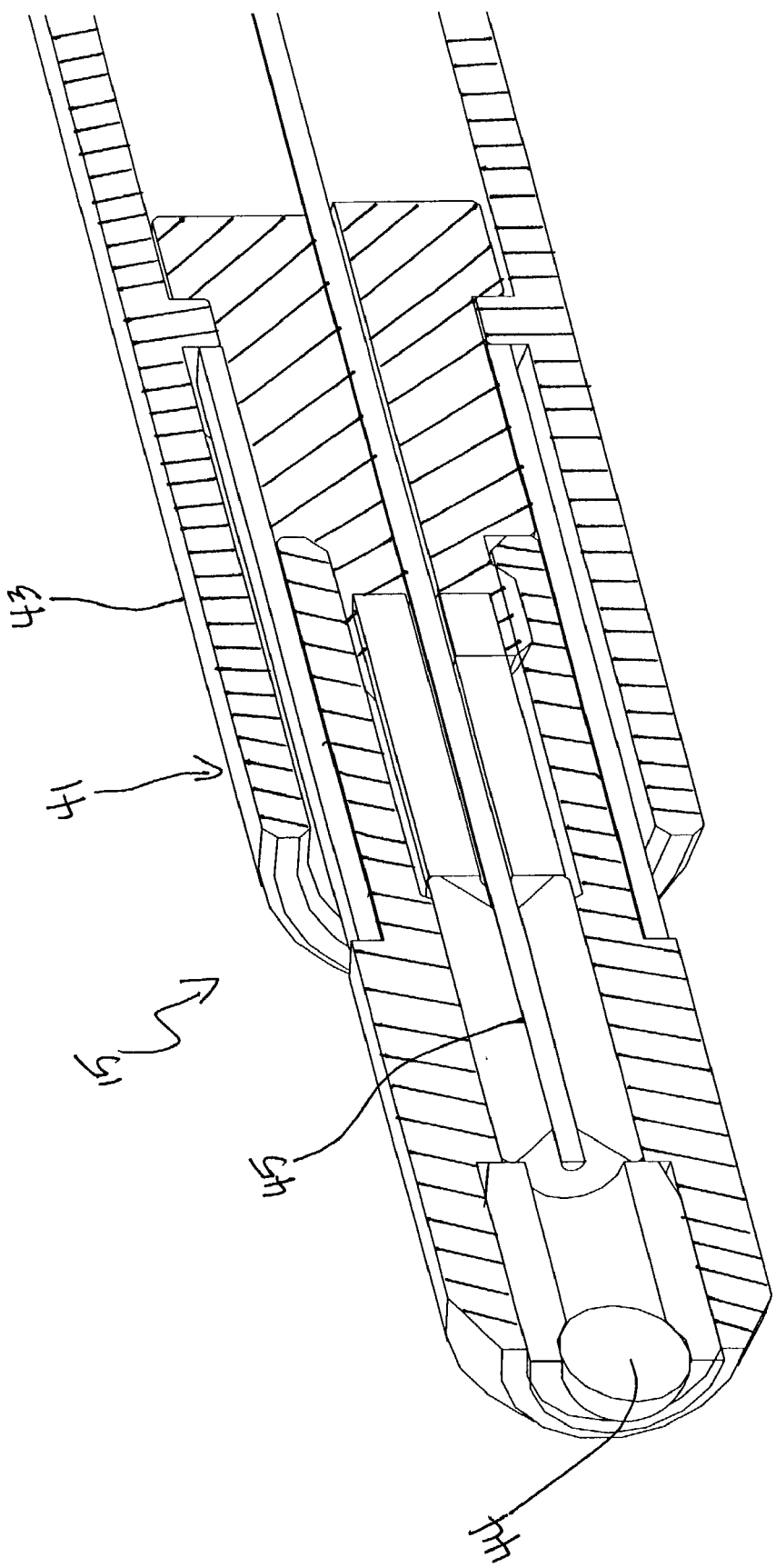
FIG. 3 is a cross-sectional view of the detector probe.

The CE system 1 includes the radiation detector 15 for detecting the radiation/light from the sample in the detection zone 27. The radiation detector 15 can include a detector probe 41, such as one referenced in U.S. patent application Ser. No. 10/060,052, entitled "Optical Detection in A Multi-Channel Bio-Separation System," filed on Jan. 28, 2002, which is assigned to BioCal Technology, Inc., the assignee of the present invention, and which is fully incorporated by reference herein. FIG. 3 is a cross-sectional view of the detector probe 41.

The detector probe 41 includes a probe housing 43 for housing a lens 44 and an emission collection fiber 45. The fluorescence emissions from the separated components or analytes at the detection zone 27 is collected through the lens 44, and directed through the emission collection fiber 45 to a detector (not shown). The capillary 2 may have transparent walls, or opaque walls provided with a transparent window to direct emissions to the lens 44. The lens 44 can be a collimation lens for collecting emissions and can have a high collection angle property (e.g., a sapphire micro-lens with index of refraction of n=1.76 from Swiss Jewel Company Model # B2.00 that has a short focal distance with a high numerical aperture (N.A.)). The lens 44 can also be an emission coupling lens (e.g., a BK-7 or Sapphire micro-lens, available from the Swiss Jewel Co.) for coupling the collimated emission light produced by the collimation lens to the emission collection fiber 45. The fluorescent light, which has a higher wavelength (e.g., 570 to 630 nm) than the excitation light (500-550 nm), is then routed by the emission collection fiber 45 (e.g., a large core optical fiber (370 μm O.D., 0.22 NA fiber, but could also be in ranges of: 100-1000 μm O.D., 0.12-0.5 NA)) to the detector (e.g., R5984 Hamamatsu photo-multiplier tube (PMT)) after going through color separation (e.g., using 570-630 nm) long pass or band pass emission filters. At the detector (PMT detector), the emission signal is filtered by a single or multiple emission filters (not shown) and can be read (detected) in a time-multiplexed (time-staggered) scheme.

Figure 4:
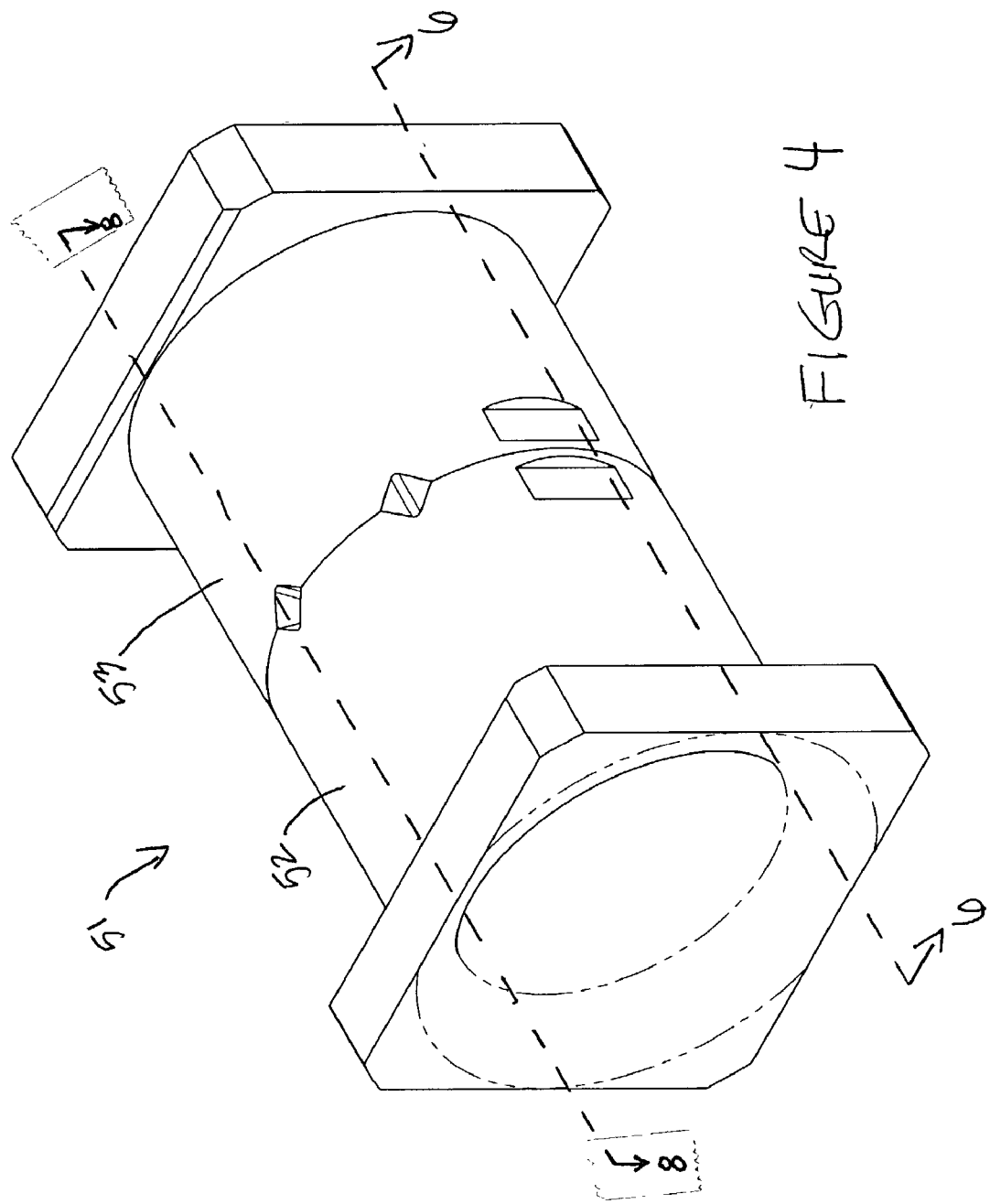
FIG. 4 is a perspective view of the alignment apparatus in accordance with one embodiment of the present invention.

Referring to FIG. 1, the CE system 1 includes an alignment apparatus or coupler 51 for positioning and aligning the excitation fiber 14 of the excitation system 31 with respect to the detection zone 27 of the capillary 2, and for optically coupling the radiation detector 15 to the detection zone 27. FIG. 4 is a perspective view of the alignment apparatus 51 in accordance with one embodiment of the present invention. The alignment apparatus 51 includes an alignment block 52 and a support block 53.

Figure 5:
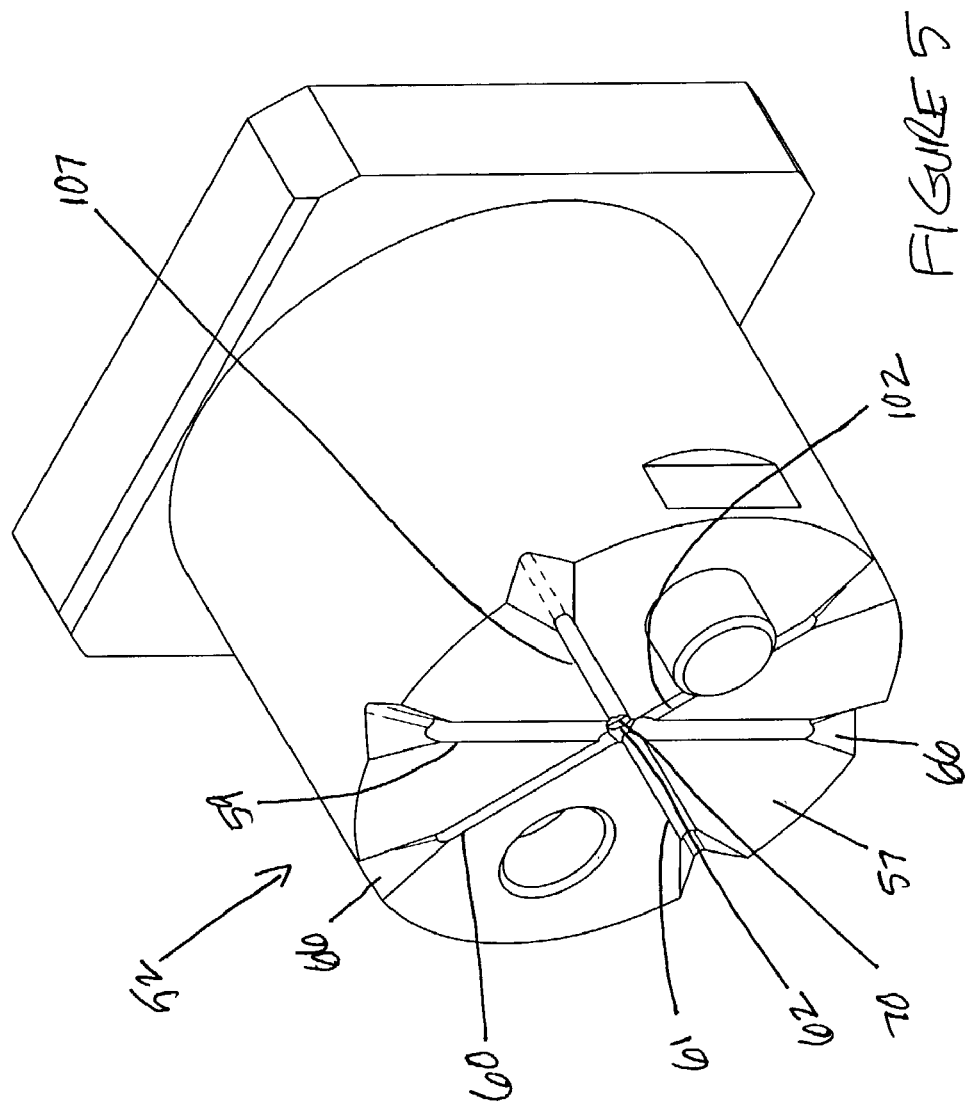
FIG. 5 is a perspective view of the alignment block in accordance with one embodiment of the present invention.
Figure 6:
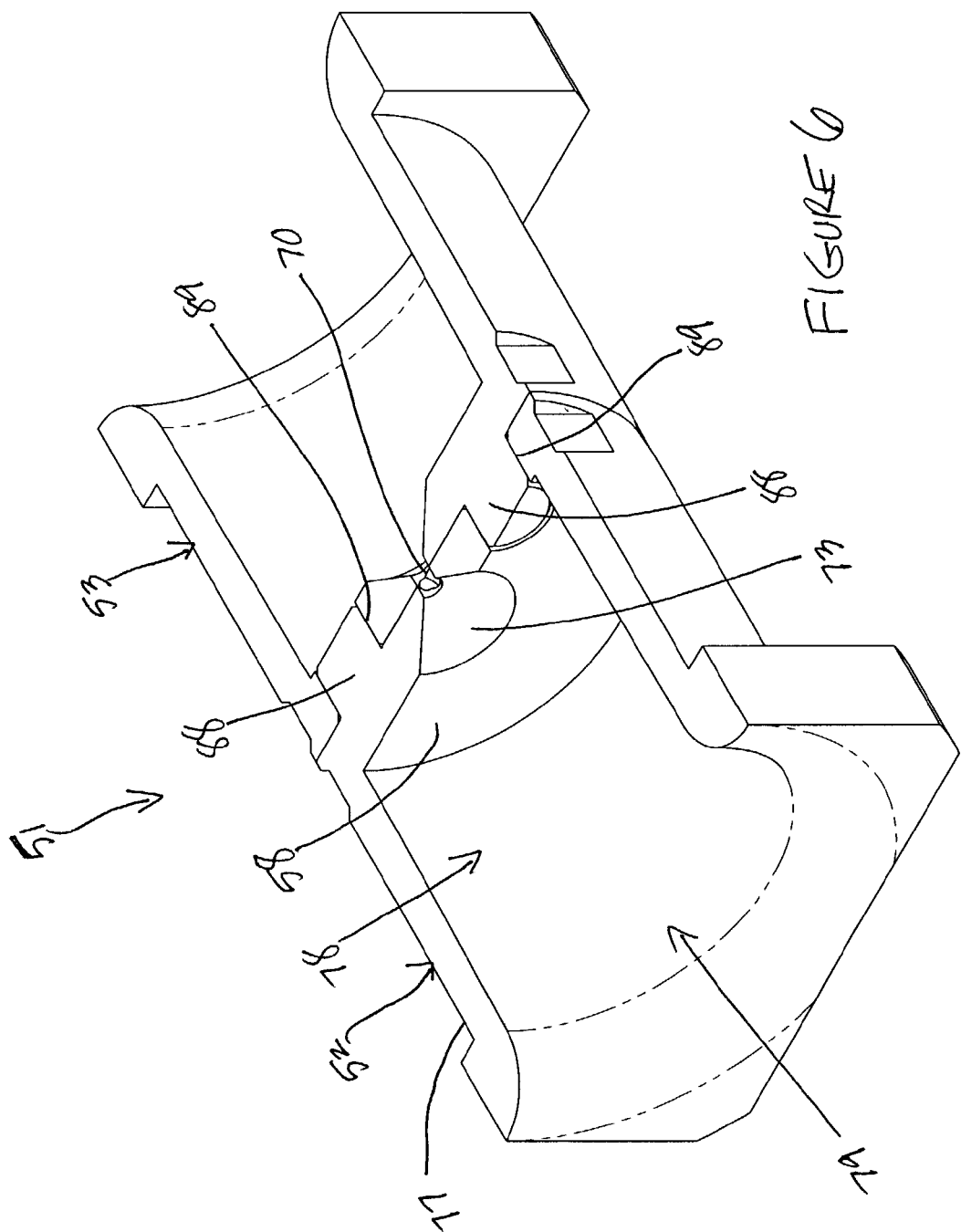
FIG. 6 is a cross-sectional view of the alignment apparatus shown in FIG. 4, taken through line 6-6.

FIG. 5 is a perspective view of the alignment block 52 in accordance with one embodiment of the present invention, and FIG. 6 is a cross-sectional view of the alignment apparatus 51 shown in FIG. 4 taken through line 6-6. The alignment block 52 includes an outer face 57 and an opposing inner face 58. In the embodiment shown in FIGS. 5 and 6, the outer and inner faces 57 and 58 have a circular shape. However, the outer and inner faces 57 and 58 can have other simple geometric shapes, such as a square shape. The outer face 57 includes a plurality of grooves or channels, such as grooves 59, 60 and 61, defined on the outer face 57. The grooves 59, 60 and 61 facilitate positioning of the capillary column 2 and the excitation fiber 14 in precise alignment to each other. The grooves 59, 60 and 61 intersect each other at a detection point 62 on the alignment block 52. The detection point 62 can be at any point on the outer face 57, such as at the center of the outer face 57, as shown in FIG.

5. A groove can span from one edge of the periphery of the outer face 57 to another edge, such as groove 59, or can span from one edge of the periphery to the detection point 62, such as grooves 60 and 61.

The grooves 59, 60 and 61 are sized and shaped to receive either the capillary 2 or the excitation fiber 14. The capillary 2 or the excitation fiber 14 can be nested within the grooves 59, 60 and 61, and positioned such that the capillary 2 or the excitation fiber 14 are precisely aligned with each other. More specifically, the grooves 60 and 61 align the excitation fibers 14 relative to the detection window 12. For example, the capillary 2 can be nested in the groove 59 such that the detection window 12 is positioned about the detection point 62. The alignment block 52 is capable of supporting one or more excitation fibers 14. In the embodiment in shown in FIG. 5, up to four excitation (or emission collection) fibers 14 can be directed at the detection point 62 where the detection window 12 is positioned. For example, a fiber can be nested in groove 60 and another fiber in groove 61. The grooves 60 and 61 guide the excitation fibers 14 to the detection window 12 until the ends of the fibers 14 butt the outer diameter of the capillary 2. The closer the fibers 14 are positioned to the analytes in the detection zone 27, the more excitation energy is directed towards the analytes and the stronger the emission signal. The grooves allow for precise intersection of the capillary and fibers centerlines. For example, a capillary having a 50 μm I.D. requires that the fiber centerline be located within 10 μm of the capillary centerline. The alignment block 52 can include a beveled opening 66 at the outer end of the grooves 59, 60 and 61. The beveled openings 66 allow the capillary 2 and the excitation fiber 14 to be more easily inserted into the grooves 59, 60 and 61.

Referring to FIGS. 5 and 6, the alignment block 52 includes an optical coupling aperture 70. The aperture 70 is a window or opening through the inner and outer faces 58 and 57 at the detection point 62. The aperture 70 allows for optical coupling between the detection window 12 on the outer face side 57, and the detection optics 44 of the radiation detector 15 on the inner face side 58 and prevents excessive leakage of scattered excitation light to be detected by the detection lens 44 and proportionally controls/reduces the Noise.

Referring to FIG. 6, the inner face 58 of the alignment block 52 interfaces with the radiation detector 15. The inner face 58 includes a lens seat 73 for positioning and aligning the radiation detector lens 44 with respect to the aperture 70. The lens seat 73 can be a conical lens seat (as shown in FIG. 6) or alternatively any configuration capable of receiving the detector lens 44, such as a spherical lens seat (not shown). The tip of the conical lens seat 73 opens to the aperture 70 to provide a passage for optically coupling the detector lens 44 with the detection window 12 on the outer face side 57.

The alignment block 52 can include a radiation detector port 77. The port 77 is adapted to receive the radiation detector 15 and to hold and align the detector optic within the lens seat 73. In the embodiment shown in FIG. 6, the port 77 is adapted to hold the detector probe 41 shown in FIG. 3. The port 77 is a barrel-shaped shell defining a cavity 78. The diameter of the cavity 78 is sized to receive the outer diameter of the probe housing 43. The barrel-shaped port 77 has two opposing ends, wherein one end of the port 77 is connected to the alignment block 52, with the inner face 58 facing the cavity 78, and the opposing end is provided as a port opening 79.

Figure 7:
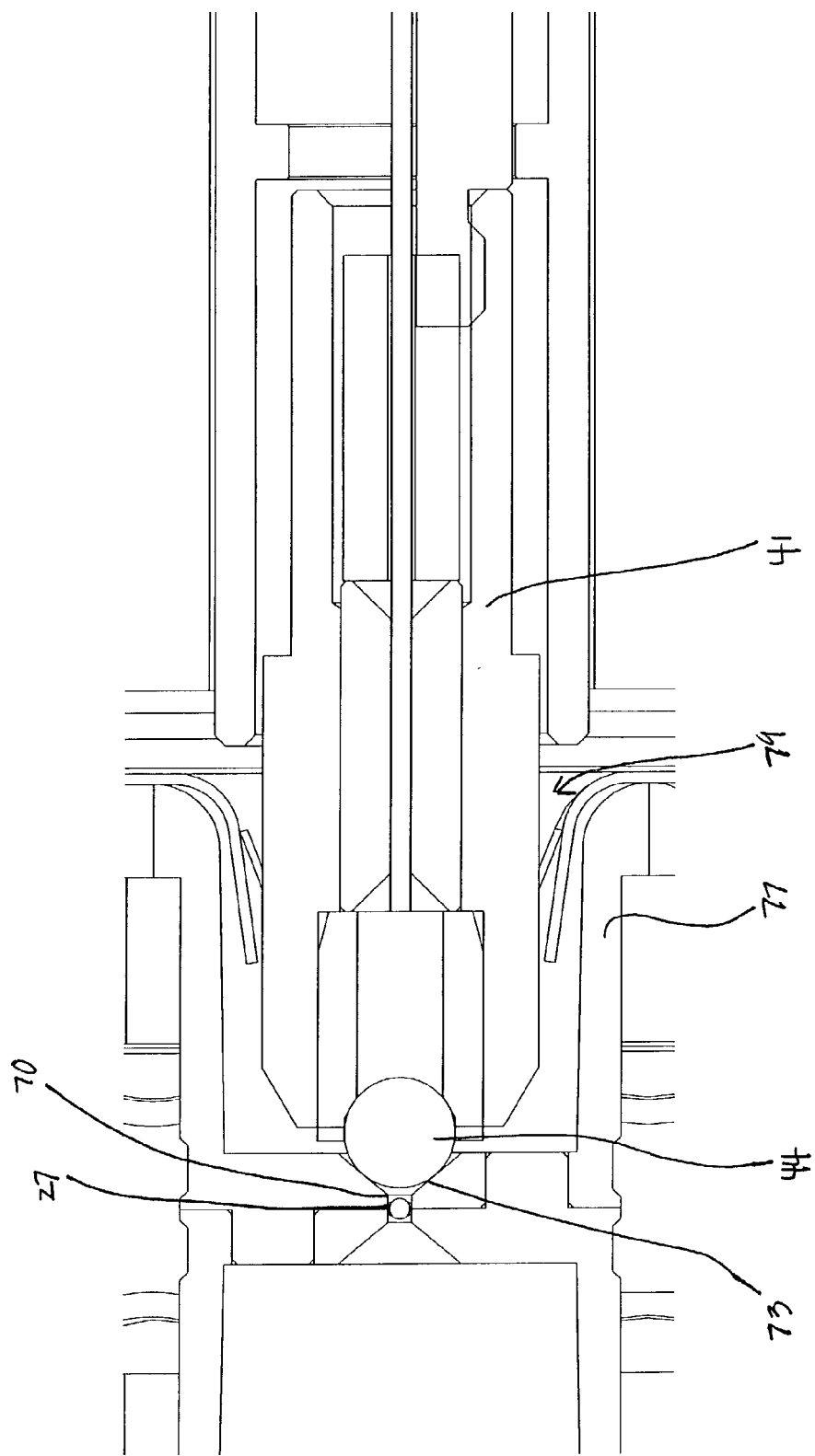
FIG. 7 is a cross-sectional view of the detector probe inserted within the detector port.

FIG. 7 is a cross-sectional view of the detector probe 41 inserted within the detector port 77. The probe 41 is inserted through the port opening 79 until the lens 44 is seated within the lens seat 73. The port shell guides the lens 44 into position within the lens seat 73 when the probe 41 is inserted within the port 77. Once seated within the lens seat 73, the lens 44 is precisely aligned with the detection zone 27. The lens 44 is optically coupled to the detection zone 27 through the aperture 70. The lens seat 73 positions and aligns the lens 44 within a predetermined distance of the detection zone 27. For example, a capillary column having a 50 μm I.D. requires that the centerline of the capillary and the optical axis of the lens must intersect within 5 μm of each other.

Referring back to FIG. 6, the alignment apparatus 51 includes the support block 53. The support block 53 supports the capillary 2 and the excitation fibers 14 within their respective grooves by engaging with the outer face 57 of the alignment block 52. The alignment block 52 includes a locking mechanism 85 for mechanically coupling the alignment block 52 to the support block 53.

In the embodiment shown in FIG. 6, the support block 53 is an identical alignment block. As shown in FIG. 6, each block 52 and 53 has the locking mechanism 85 having a pair of male and female parts 88 and 89. The male part 88 is a pin and the female part 89 is a catch sized and shaped to receive the pin 88. FIG. 6 shows the alignment block 52 engaged with the support block 53. To engage the two blocks 52 and 53 together to form the alignment apparatus 51, the pin 88 of the alignment block 52 is mated with the catch 89 of the support block 53, while the pin 88 of the support block 53 is mated with the catch 89 of the alignment block 52. The pin 88 and the catch 89 facilitate alignment of the two blocks 52 and 53 for mating. Since the two blocks 52 and 53 are identical, the female part 89 of one block is sized and shaped to receive the male part 88 of the other block. The pin 88 and the catch 89 are a press fit to provide a centering effect that removes the diameters of the pin 88 and the catch 89 from the tolerance stacks affecting the position of the capillary 2, the fibers 14, and the lens 44. The press fit of the pin 88 and the catch 89 also allows for assembly of the alignment apparatus 51 without use of fasteners.

Since the alignment block 52 and the support block 53 mate at a plane coincident with the axis of the capillary 2, the alignment block 52 and the support structure block 53 can be attached radially to the capillary 2, thus precluding the need to string the alignment apparatus 51 onto the capillary 2. This allows the alignment apparatus 51 to be attached to the capillary 2 after end fittings have been fitted to the capillary 2.

FIG. 8 is a cross-sectional view of the alignment apparatus 51 shown in FIG. 2 taken along line 8-8. FIG. 8 shows the alignment block 52 in engagement with the support block 53. Once the blocks 52 and 53 have mated, a groove of the alignment block 52 interfaces with a corresponding groove of the support block 53 to form a shaft into which the capillary 2 or the excitation fibers 14 can be positioned into. The locking mechanism 85 allows the corresponding grooves to precisely align to form the shaft. FIG. 8 shows, for example, a shaft 92 for receiving the capillary 2. The capillary 2 is shown positioned within the channel 92. The plurality of shafts are sized to receive the outer diameter of either the capillary 2 or the excitation fiber 14. The shafts facilitate positioning and alignment of the detection window 12 of the capillary 2 and the excitation fibers 14 with each other. Furthermore, FIG. 2 shows a plurality of shaft openings 93 defined by the beveled openings 66 of the plurality of grooves 59, 60 and 61. The shaft openings 93 allow the capillary 2 and the excitation fibers 14 to be more easily inserted into the shafts.

The support block can have any configuration which allows support of the capillary and the excitation fibers within the plurality of grooves. For example, the support block can be a simple plate structure having a face capable of engaging with the outer face of the alignment block (not shown). The alignment block can also be provided with any locking mechanism that allows for securely coupling the alignment block with the support block, such as screwing or gluing the two blocks together.

The alignment apparatus 51 of the present invention is capable of aligning multiple excitation fibers 14 relative to a single capillary 2. Additionally, the alignment apparatus 51 of the present invention is capable of optically coupling one or two detection lenses 44 with a single capillary 2. In the embodiment of the alignment apparatus 51 shown in FIG. 4 and in the embodiment of the alignment block 52 shown in FIG. 5, the alignment apparatus 51 can support up to four excitation fibers 14 to one capillary 2, and can couple up to two micro-ball lenses 44 with one capillary 2. This arrangement allows for two emission detection lenses 44 to be coupled from the two sides of the capillary 2 (180 degrees with respect to each lens) to increase the emission collection light and enhance the detection sensitivity. The same approach could also be applied in the case of using two separate excitation fibers (for two different excitation wavelengths) and detection of dual wavelengths by two detection lenses from one capillary.

Figure 9A:
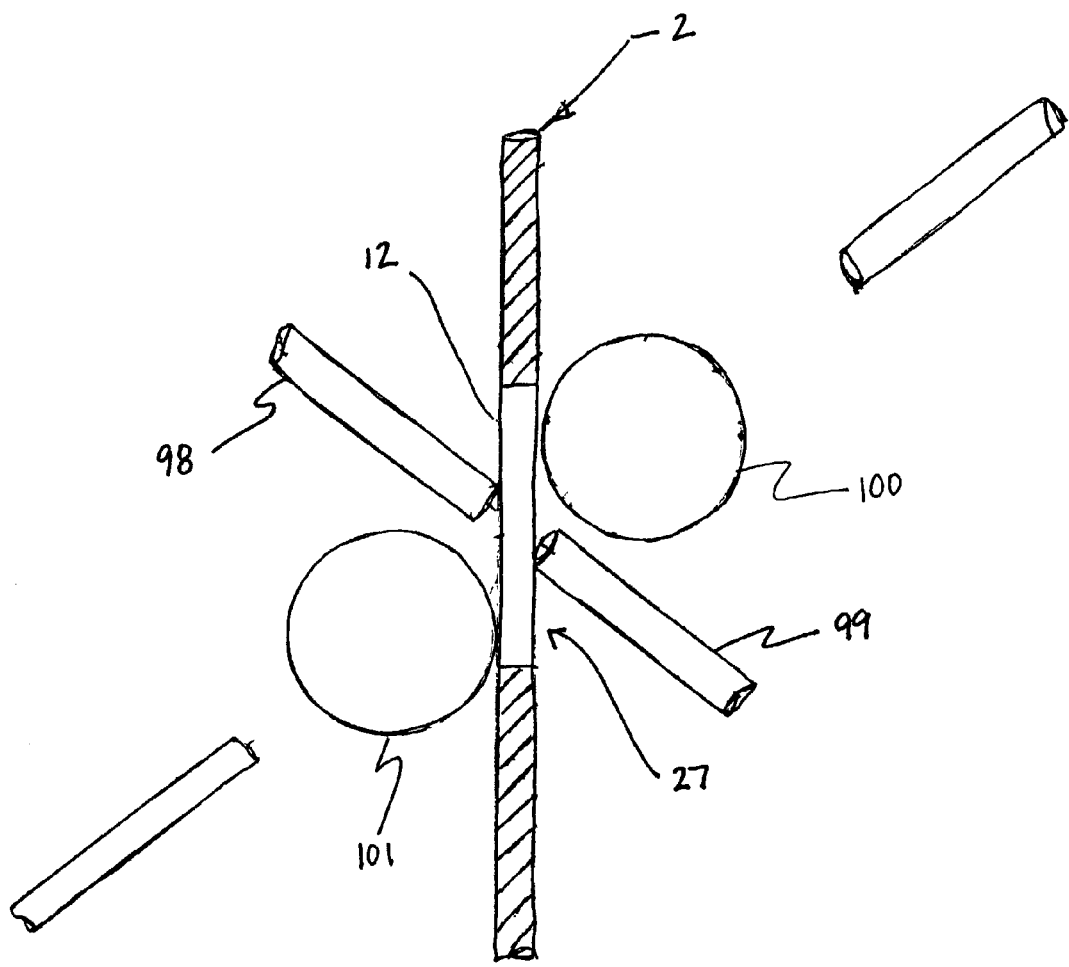
FIG. 9A is a simplified drawing of a fluorescence detection scheme employing two excitation fibers and two detection lenses.

FIGS. 9A through 9D illustrate example detection schemes that can be employed with the alignment apparatus 51 of the present invention. FIG. 9A is a simplified drawing of a fluorescence detection scheme employing two excitation fibers 98 and 99, and two detection lenses 100 and 101. The capillary 2 can be nested in the groove 59 with the detection window 12 positioned about the detection point 62 (as shown in FIG. 5). The fiber 98 can be located in the groove 60 and the fiber 99 can be located in a groove 102. The fibers 98 and 99 deliver excitation light from the radiation source 13 to the analytes within the detection window 12 of the capillary 2. The lens 100 can be located within the lens seat 73 of the alignment block 52, and the lens 101 can be located within the lens seat 73 of the support block 53. Both lenses 100 and 101 are optically coupled to the detection zone 27. The lenses 100 and 101 collimate the fluorescence signal from the detection zone 27 and direct the signal to the PMT's. Use of the two lenses 100 and 101 permit a multi-color fluorescence optical detection scheme.

Figure 9B:
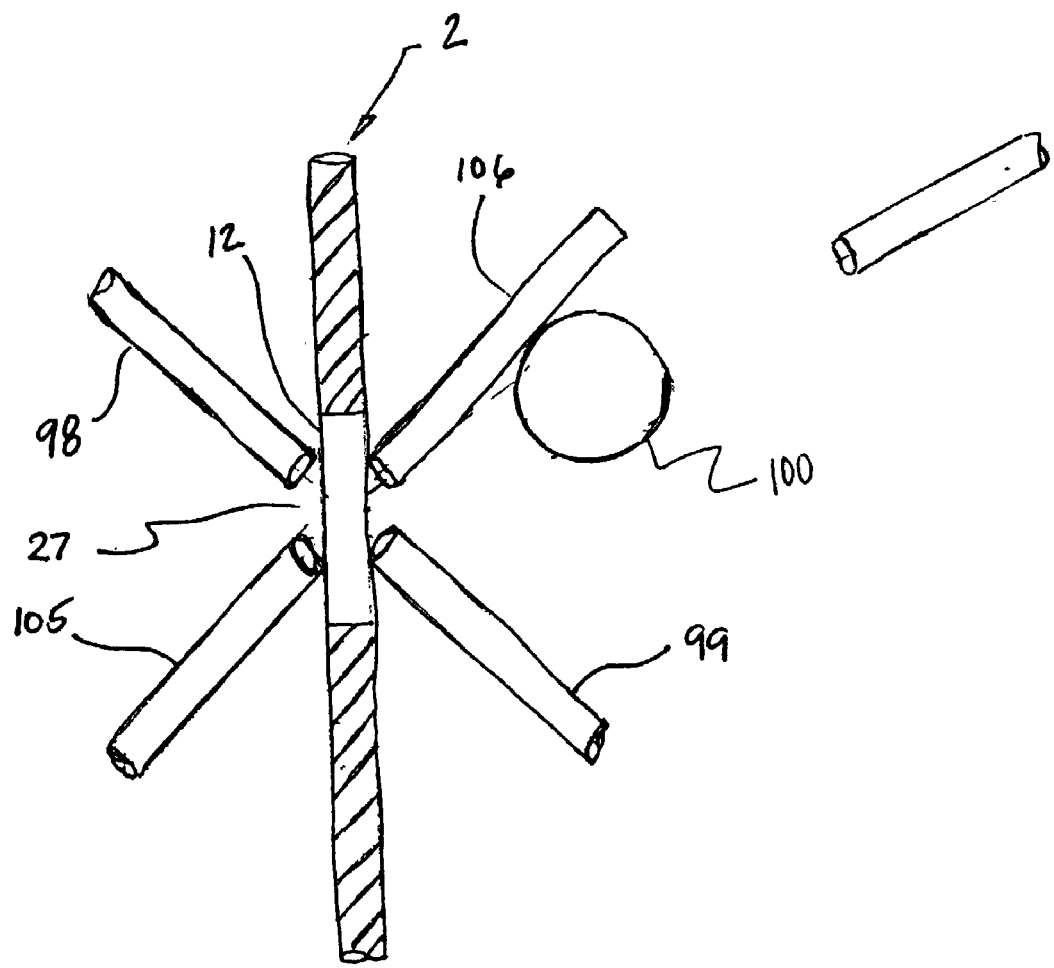
FIG. 9B is a simplified drawing of a fluorescence detection scheme employing four excitation fibers and a single detection lens.

FIG. 9B is a simplified drawing of a fluorescence detection scheme employing four excitation fibers 98, 99, 105 and 106, and the detection lens 100. The capillary 2 can be nested in the groove 59 with the detection window 12 positioned about the detection point 62 (as shown in FIG. 5). The fiber 98 can be nested in the groove 60, the fiber 99 can be nested in the groove 102, the fiber 105 can be nested in the groove 61 and the fiber 106 can be nested in a groove 107. The fibers 98, 99, 105 and 106 deliver excitation light from the radiation source 13 to the analytes within the detection window 12 of the capillary 2. The lens 100 can be seated within the lens seat 73 of the alignment block 52 or within the lens seat 73 of the support block 53. The lens 100 is optically coupled to the detection zone 27. The lens 100 collimates the fluorescence signal from the detection zone 27 and directs the signal to the PMT's via fibers.

The excitation system can be provided in a light probe (not shown) for use in an absorbance optical detection scheme. The light probe includes a light source, a light transmitting fiber, and a micro-ball lens. Light from the light source (e.g., LED, laser, D2, Xenon or Mercury lamps) is directed through the light transmitting fiber to the micro-ball lens. The light probe can be inserted into the port 77 of the alignment block 52, such that when the light probe is inserted within the port 77, the micro-ball lens is seated within the lens seat 73 of the alignment block 52. Once within the lens seat 73, the micro-ball lens can direct the light to the detection window 12 through the aperture 70.

Figure 9C:
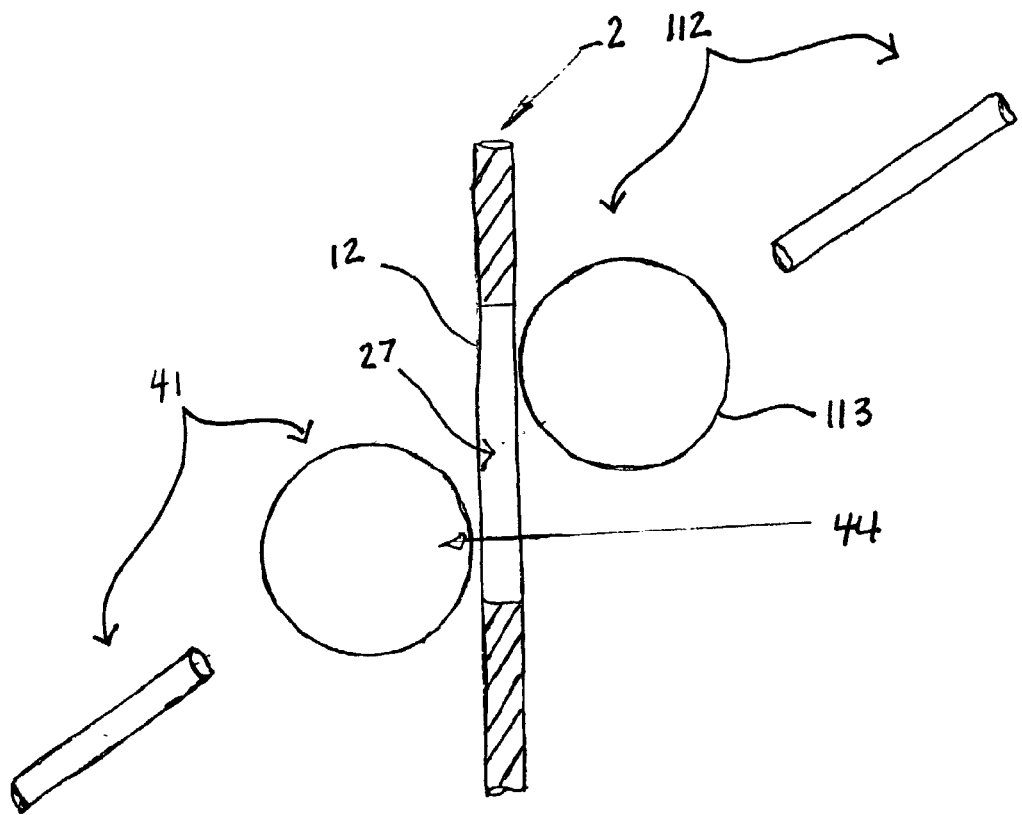
FIG. 9C is a simplified drawing of an absorbance optical detection scheme employing a light probe and the detection probe.

FIG. 9C is a simplified drawing of an absorbance optical detection scheme employing a light probe 112 and the detection probe 41. The capillary 2 can be nested in the groove 59 with the detection window 12 positioned about the detection point 62 (shown in FIG. 5). Each of the light probe 112 and the detection probe 41 can be inserted in the port 77 of either the alignment block 52 or the support block 53. A micro-ball lens 113 of the light probe 112 can be seated in the lens seat 73 of either the alignment block 52 or the support block 53. The lens 113 is optically coupled to the detection zone 27 through the aperture 70. The lens 113 can direct light from the light source to the detection window 12. The micro-ball lens 44 of the detection probe 41, therefore, can be seated in the other lens seat 73 of the alignment apparatus 51. The lens 44 is optically coupled to the detection zone 27 through the aperture 70. The lens 44 can detect the signal from the detection zone 27 and can direct the signal to a detector (e.g., PMT).

Figure 9D:
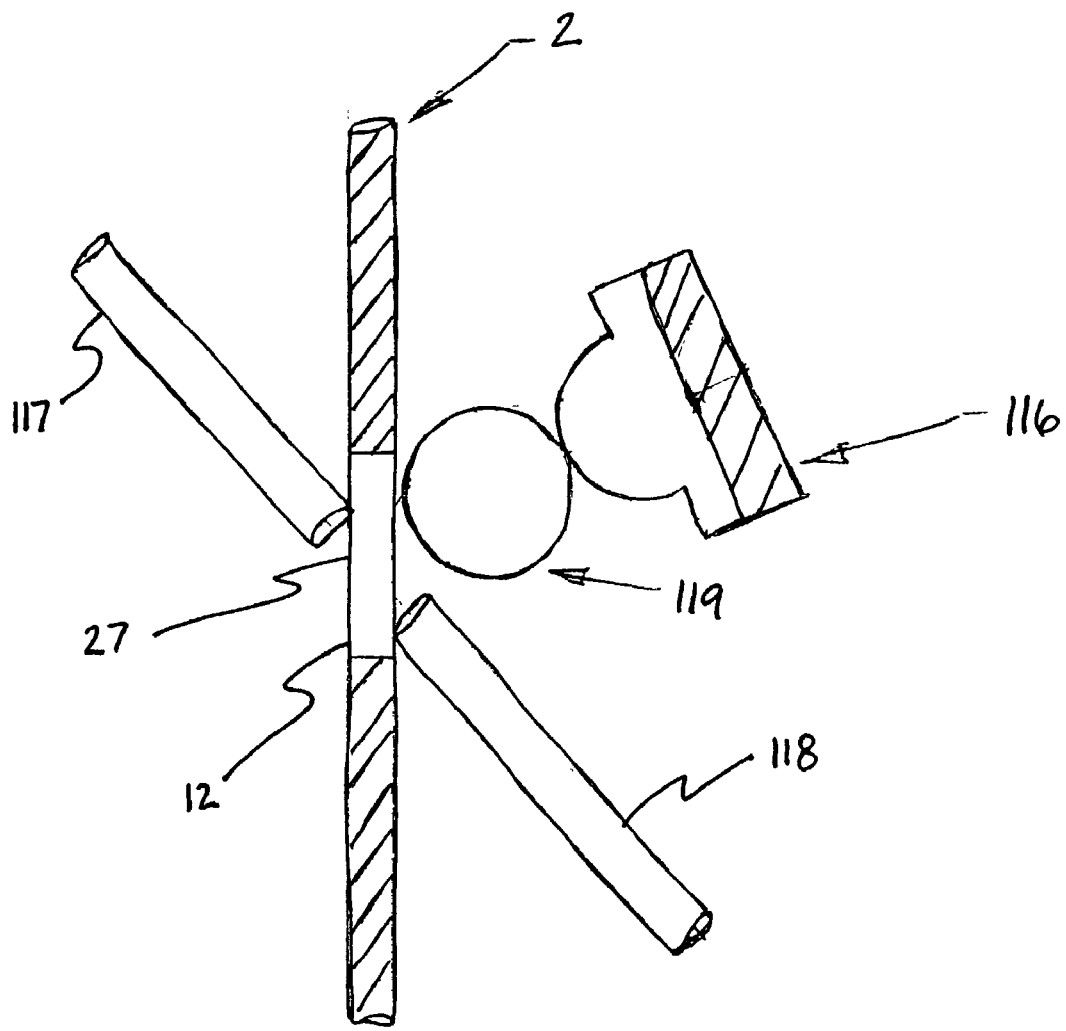
FIG. 9D is a simplified drawing of a detection scheme employing a surface mount LED light source and two detection fibers.

FIG. 9D is a simplified drawing of a detection scheme employing a surface mounted LED light source 116 and two detection fibers 117 and 118. The capillary 2 can be nested in the groove 59 with the detection window 12 positioned about the detection point 62 (shown in FIG. 5). The surface mounted LED light source 116 provides excitation light that is directed to a coupling micro-ball lens 119. The lens 119 is seated in the lens seat 73, such that the lens 119 optically couples the light to the detection window 12 through the aperture 70. The fibers 117 and 118 can be nested in the grooves 60 and 102, for example. The fibers 117 and 118 direct signals from the detection zone 27 to a detector (e.g., PMT).

The alignment block 52 of the present invention can be formed from any material that does not significantly fluoresce at critical wavelengths, such as aluminum, stainless steel, copper, platinum, Gold, silver, glass, ceramic, zinc, and non-fluorescing plastics such as ESD. The materials thus minimize the background noise, and therefore increase the detection sensitivity of the CE system 1.

The simple geometric features of the alignment block 52 of the present invention allow the alignment block 52 to be fabricated by a variety of fabrication methods well known in the art, such as die-casting, tooling and injection molding. Accordingly, the simple geometric features allow the alignment block 52 to be producible at a low cost.

The alignment apparatus 51 of the present invention also allows for easy assembly of the apparatus 51. In the embodiment shown in FIG. 4, the components of the alignment apparatus 51 is comprised only of the two identical blocks 52 and 53. Each block 52 and 53 has the relatively simple locking mechanism 85. Assembly of alignment apparatus 51 requires only to align the respective pins 88 and catches 89 of the two blocks 52 and 53 and to simply snap the two identical blocks 52 and 53 together.

The relatively simple geometric features of the alignment block 52 and the relative ease in assembling the alignment apparatus 51 allow the alignment apparatus 51 to be employed in a variety of environments. For example, the alignment apparatus 51 can be incorporated in a relatively mobile CE system for use in an environment where use of a larger CE-instrument is not practical, such as a laboratory setting. The mobile CE system can simply include the alignment apparatus 51 for coupling and aligning a single capillary with the excitation system 31 and radiation detector 15. Multiple alignment apparatuses 51 can also be fitted along the length of the capillary 2 for zone detection.

Additionally, a plurality of alignment apparatuses 51 (shown in FIG. 4) can be provided in a linear array for integration into a multi-capillary CE-instrument. FIG. 10 is a perspective view of a linear array support bracket 122 in accordance with one embodiment of the present invention. The support bracket 122 has an I-shaped configuration having a plurality of holes 123 defined through a middle flange 124. The plurality of holes 123 are sized and shaped to receive the outer diameter of the alignment block 52 (shown in FIG. 5).

FIG. 11 is a perspective view of an assembly 125 of a linear array of alignment blocks 52. The assembly 125 includes the support bracket 122 holding and positioning a plurality of alignment blocks 52 in a linear array. Each alignment block 52 is removeably supported within one of the holes 123 of the support bracket 122. The support bracket 122 allows for one or more alignment blocks 52 to be fitted and removed depending upon the particular requirements of the application.

Figure 12:
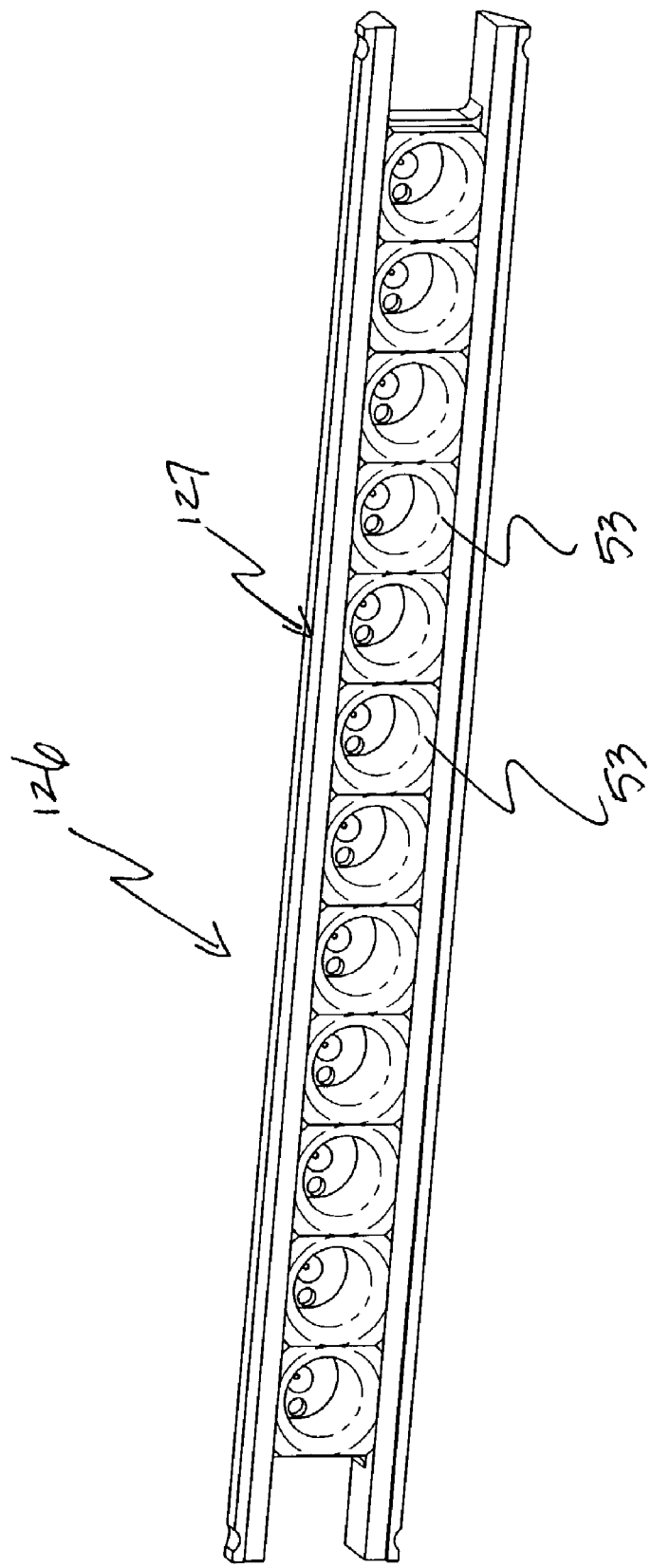
FIG. 12 is a perspective view of an assembly of a linear array of support blocks.

FIG. 12 is a perspective view of an assembly 126 of a linear array of support blocks 53. The assembly 126 includes another support bracket 127 for holding and positioning the plurality of support blocks 53 in a linear array to provide the assembly 126 of the liner array of support blocks 53. Each support block 53 is removeably supported within one of the holes of the support bracket 127. The support bracket 127 allows for one or more alignment blocks 53 to be fitted and removed depending upon the particular requirements of the application.

Figure 13:
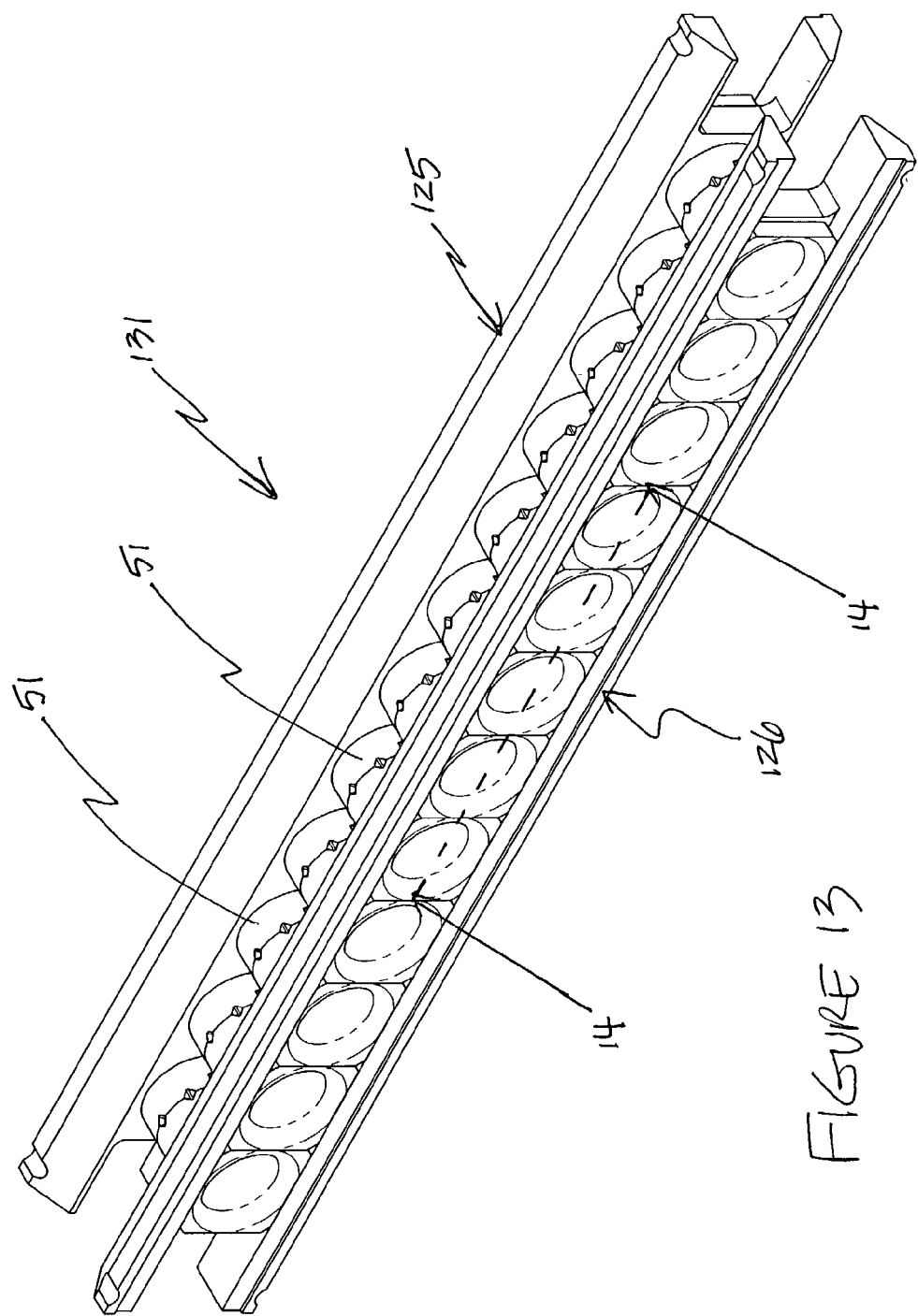
FIG. 13 is a perspective view of an assembly of a linear array of alignment apparatuses.
Figure 14:
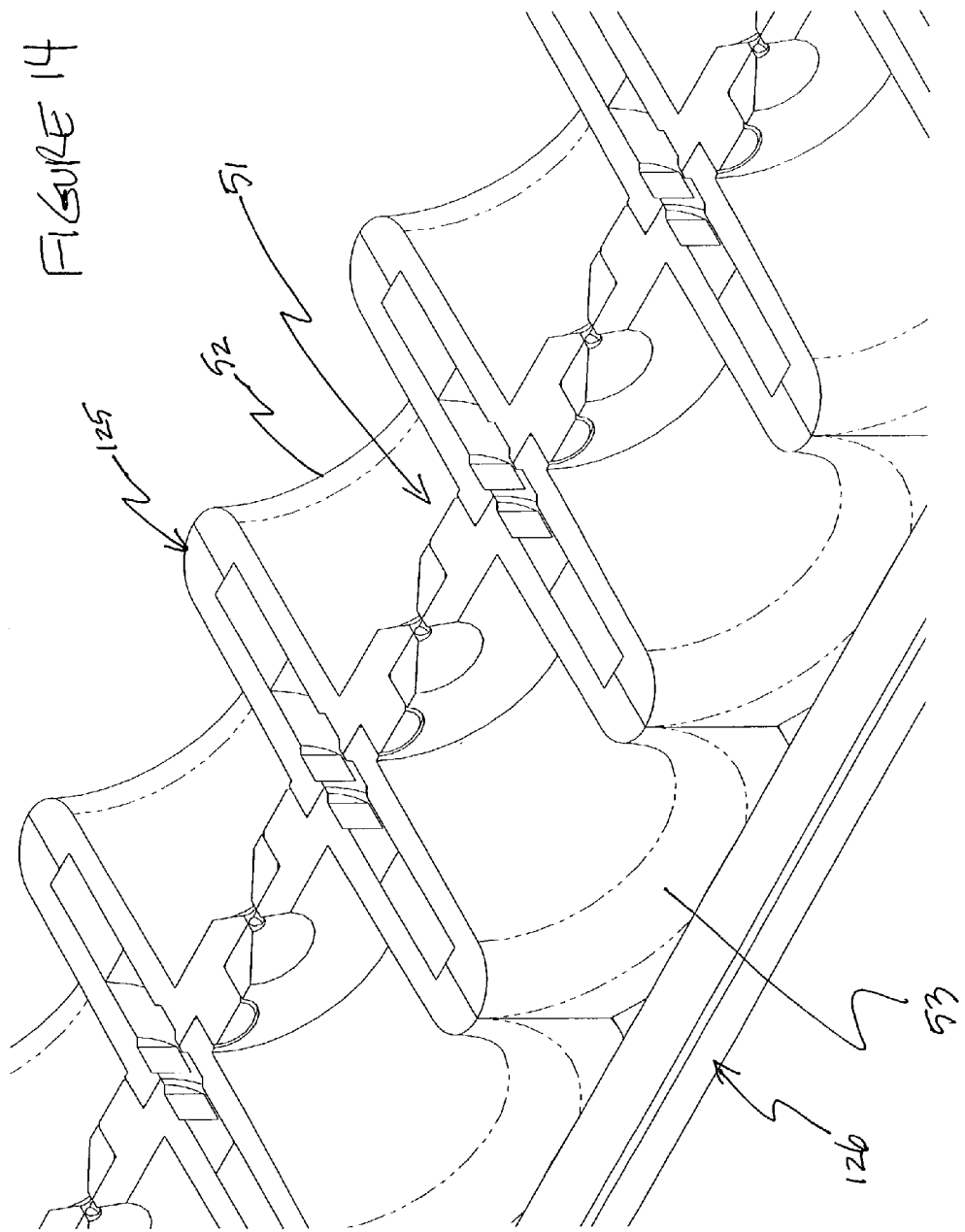
FIG. 14 is a cross-sectional view of the assembly of the linear array of alignment apparatuses shown in FIG. 13, taken through line 14-14.

FIG. 13 is a perspective view of an assembly 131 of a linear array of alignment apparatuses 51. The assembly 131 includes the assembly 125 (shown in FIG. 11) and the assembly 126 (shown in FIG. 12) in engagement with each other to form the linear array of alignment apparatuses 51. FIG. 14 is a cross-sectional view of the assembly 131 of the linear array of alignment apparatuses shown in FIG. 13, taken through line 14-14. The assembly 131 can be assembled by mating one of the plurality of alignment blocks 52 of the assembly 125 with a corresponding support block 53 of the assembly 126 (as detailed herein) until all of the plurality of alignment blocks 52 are mated with their corresponding support blocks 53. Each alignment apparatus in the array is capable of providing optical shielding to minimize cross talking across other alignment apparatuses 51 in the array.

The assembly 131 allows for multi-capillary CE. Each alignment apparatus 51 of the assembly 131 can support one capillary 2. Furthermore, each alignment apparatus 51 of the assembly 131 can locate one or more excitation fibers 14 for the capillary 2 and can optically couple one or two lenses to the detection window 12 of the capillary 2.

The assembly 131 can be incorporated into a multi-capillary CE-instrument (not shown). Reference is made to U.S. patent application Ser. No. 10/060,052, entitled "Optical Detection In A Multi-Channel Bio-Separation System," filed on Jan. 28, 2002, which is commonly assigned to BioCal Technology, Inc., the assignee of the present invention, which is fully incorporated by reference herein, and to U.S. patent application Ser. No. 10/059,993 entitled "Multi-Channel Bio-Separation Cartridge," filed on Jan. 28, 2002, which is commonly assigned to BioCal Technology, Inc., the assignee of the present invention, and which is fully incorporated by reference herein.

FIG. 15 is an exploded perspective view of a mid-section body of a multi-capillary cartridge 137, the assembly 125 of the linear array of alignment blocks and the assembly 126 of the linear array of support blocks. The assemblies 125 and 126 can be engaged with each other at a section 138 of the mid-section body of the multi-capillary cartridge 137. The assembly including the mid-section body 137 incorporated with the assemblies 125 and 126 can be further incorporated with the multi-capillary CE-system (not shown). The assembly 131 (shown in FIG. 13) allows for positioning one or more capillaries in a linear array within a particular design requirement, such as 9 mm or less (9 mm is the pitch distance for a standard 96-well micro-titer plate).

In another embodiment of the present invention (not shown), the plurality of alignment blocks and the plurality of support blocks are integral or unitary with the linear array brackets.

What is claimed is:

1. An apparatus for aligning a capillary, for supporting a sample, with respect to a sample analysis system including a fiber, the apparatus comprising:
   an alignment block having an outer face and an inner face;
   a plurality of grooves defined on the outer face, wherein the plurality of grooves intersect about at a detection point on the alignment block, wherein each of the plurality of grooves is sized and shaped to nest at least one of the capillary or the fiber; and
   a support block having a face with an area similar to the outer face, wherein a plurality of complementary grooves are defined on the face, wherein the plurality of complementary grooves intersect about at a point on the support block, wherein each of the plurality of complementary grooves is sized and shaped to nest at least one of the capillary or the fiber, and wherein the face mates against the outer face to clamp the capillary or the fiber within the plurality of grooves and the plurality of complementary grooves.

2. The apparatus of claim 1, wherein the plurality of grooves includes a capillary groove and one or more fiber grooves, wherein the capillary groove is sized and shaped to nest the capillary and each of the one or more fiber grooves is sized and shaped to nest one fiber, wherein when the capillary is nested within the capillary groove and the fiber is nested within the fiber groove the fiber is substantially precisely aligned with the capillary.

3. The apparatus of claim 2, wherein when the capillary is nested within the capillary groove and the fiber is nested within the fiber groove the centerline of the capillary is substantially precisely intersecting with the centerline of the fiber.

4. The apparatus of claim 1, further comprising a locking mechanism for engaging the alignment block with the support block.

5. The apparatus of claim 4, wherein the locking mechanism comprises a first pair of male and female parts provided on the outer face and a second pair of male and female parts provided on the support block, wherein the alignment block is engaged to the support block by mating the male part of the alignment block with the female part of the support block and mating the male part of the support block with the female part of the alignment block.

6. The apparatus of claim 5, wherein the male part includes a pin, and wherein the female part includes a hole adapted to receive the pin in a press fit.

7. The apparatus of claim 1, wherein the support block is provided as an identical alignment block, and wherein the grooves of each of the support block and the alignment block supports one half of a cross-section of the capillary or the fiber.

8. The apparatus of claim 1, further comprising:
an aperture defined through the outer and inner faces at the detection point; and
a lens seat provided on the inner face for seating a lens element of the sample analysis system, wherein the lens seat opens to the detection point.

9. The apparatus of claim 8, wherein when the lens element is seated within the lens seat the lens element is optically coupled with the capillary through the aperture.

10. The apparatus of claim 8, wherein the alignment block includes a port at the inner face to facilitate seating the lens element within the lens seat.

11. The apparatus of claim 10, wherein the port is a shell structure defining a cavity, wherein the inner face is disposed within the cavity.

12. An apparatus for aligning a capillary and a fiber, for supporting a sample, with respect to a sample analysis system including a lens element, the apparatus comprising:
an alignment block having an outer face and an inner face;
a capillary groove and a fiber groove defined on the outer face, wherein the capillary groove and the fiber groove intersect about at a detection point on the alignment block, wherein the capillary groove is sized and shaped to nest the capillary, and the fiber groove is sized and shaped to nest the fiber, and wherein when the capillary is nested within the capillary groove and the fiber is nested within the fiber groove the fiber is substantially precisely aligned with the capillary;
an aperture defined through the outer and inner faces at the detection point;
a lens seat provided on the inner face for seating the lens element, wherein the lens seat opens to the detection point; and
a support block having a face with an area similar to the outer face, wherein complementary grooves are defined on the face, wherein the complementary grooves intersect about at a point on the support block, wherein the complementary grooves are sized and shaped to nest the capillary and fiber, and wherein the face mates against the outer face to clamp the capillary and fiber within the capillary groove and fiber groove, and the complementary grooves.

13. The apparatus of claim 12, wherein when the lens element is seated within the lens seat the lens element is optically coupled with the capillary through the aperture.

14. The apparatus of claim 12, wherein the alignment block includes a port at the inner face to facilitate seating the lens element within the lens seat.

15. The apparatus of claim 14, wherein the port is a shell structure defining a cavity, wherein the inner face is disposed within the cavity.

16. The apparatus of claim 12, wherein when the capillary is nested within the capillary groove and the fiber is nested within the fiber groove the centerline of the capillary is substantially precisely intersecting with the centerline of the fiber.

17. The apparatus of claim 12, further comprising a locking mechanism for engaging the alignment block with the support block.

18. An alignment coupling for supporting a capillary, a fiber and detector probe having a lens element, comprising:
an alignment block, which comprises:
an outer face and an inner face;
a plurality of grooves defined on the outer face, wherein the plurality of grooves intersect about at a detection point, wherein each of the plurality of grooves is sized and shaped to nest at least one of the capillary or the fiber, wherein the grooves each supports one half of a cross-section of the capillary or the fiber; an aperture defined through the outer and inner faces at the detection point;
a lens seat provided on the inner face for seating the lens element, wherein the lens seat opens to the detection point; and
a port at the inner face adapted to receive the detector probe, wherein the port guides the lens element of the detector probe within the lens seat; and
a support block, which comprises:
a face with an area similar to the outer face;
a plurality of complementary grooves defined on the face, wherein the plurality of complementary grooves intersect about at a point on the support block, wherein each of the plurality of complementary grooves is sized and shaped to nest at least one of the capillary or the fiber, and wherein the face mates against the outer face to clamp the capillary or the fiber within the plurality of grooves and the plurality of complementary grooves.

19. A bio-separation system comprising:
a capillary, a fiber and a lens element; and
an alignment apparatus comprising:
an alignment block having an outer face and an inner face;
a plurality of grooves defined on the outer face, wherein the plurality of grooves intersect about at a detection point on the alignment block;
the plurality of grooves includes a capillary groove and a fiber groove, wherein the capillary groove is sized and shaped to nest the capillary and the fiber groove is sized and shaped to nest the fiber, wherein when the capillary is nested within the capillary groove and the fiber is nested within the fiber groove the fiber is substantially precisely aligned with the capillary;
an aperture defined through the outer and inner faces at the detection point;
a lens seat defined on the inner face for seating the lens element, wherein the lens seat opens to the detection point;
a support block having a face with an area similar to the outer face, wherein a plurality of complementary grooves are defined on the face, intersecting about at a point on the support block, wherein the plurality of complementary grooves includes a complementary capillary groove and a complementary fiber groove, where the complementary capillary groove is sized and shaped to nest the capillary and the complementary fiber groove is sized and shaped to nest the fiber, and wherein the face mates against the outer face to clamp the capillary and the fiber within the capillary and fiber grooves and the complementary capillary and fiber grooves; and
a locking mechanism for mating the alignment block and the support block in a press fit.

20. The bio-separation system of claim 19, wherein the capillary groove is capable of positioning a detection window of the capillary substantially about the detection point, and the fiber groove is capable of precisely aligning the fiber at a predetermined distance from the detection window.

21. The bio-separation system of claim 19, wherein when the lens element is seated within the lens seat the lens is optically coupled with the detection window through the aperture.

22. An assembly for aligning a plurality of capillaries, a plurality of fibers, and a plurality of lens elements with respect to each other, the assembly comprising:
a plurality of alignment apparatuses, each of the plurality of alignment apparatuses comprising:
an alignment block having an outer face and an inner face;
a plurality of grooves defined on the outer face, wherein the plurality of grooves intersect about at a detection point on the alignment block;
the plurality of grooves includes a capillary groove and a fiber groove, wherein the capillary groove is sized and shaped to nest the capillary and the fiber groove is sized and shaped to nest the fiber, wherein when the capillary is nested within the capillary groove and the fiber is nested within the fiber groove the fiber is substantially precisely aligned with the capillary;
an aperture defined through the outer and inner faces at the detection point;
a lens seat provided on the inner face, wherein the lens seat is adapted to seat the lens element, wherein the lens seat opens to the detection point;
a support block having a face with an area similar to the outer face, wherein a plurality of complementary grooves are defined on the face, intersecting about at a point on the support block, wherein the plurality of complementary grooves includes a complementary capillary groove and a complementary fiber groove, where the complementary capillary groove is sized and shaped to nest the capillary and the complementary fiber groove is sized and shaped to nest the fiber, and wherein the face mates against the outer face to clamp the capillary and the fiber within the capillary and fiber grooves and the complementary capillary and fiber grooves; and
a locking mechanism for mating the alignment block and the support block in a press fit; and
an apparatus bracket for supporting the plurality of alignment apparatuses in a linear array, the apparatus bracket having a flange and linear array of holes defined through the flange; wherein each hole is adapted to support one of the plurality of alignment apparatuses.

23. The assembly of alignment apparatuses of claim 22, wherein each of the plurality of alignment apparatuses are removeably fitted within each of the holes.

24. The assembly of alignment apparatuses of claim 22, wherein each of the plurality of alignment apparatuses are integral with the flange within the holes.

25. The assembly of alignment apparatuses of claim 22, wherein the apparatus bracket comprises an alignment block bracket having a plurality of alignment block holes adapted to support the plurality of alignment blocks in a linear array, and a support block bracket having a plurality of support block holes adapted to support the plurality of support blocks in a linear array.

* * * * *